(12) United States Patent
Kneteman et al.

(10) Patent No.: US 7,161,057 B2
(45) Date of Patent: *Jan. 9, 2007

(54) ANIMAL MODEL HAVING A CHIMERIC HUMAN LIVER

(75) Inventors: Norman M. Kneteman, Edmonton (CA); D. Lorne Tyrrell, Edmonton (CA); David F. Mercer, Edmonton (CA)

(73) Assignee: KMT Hepatech, Inc., Alberta (CA)

(*) Notice: Subject to any disclaimer, the term of this patent is extended or adjusted under 35 U.S.C. 154(b) by 426 days.

This patent is subject to a terminal disclaimer.

(21) Appl. No.: 10/243,087

(22) Filed: Sep. 12, 2002

(65) Prior Publication Data

US 2003/0115616 A1 Jun. 19, 2003

Related U.S. Application Data

(63) Continuation-in-part of application No. PCT/CA01/00350, filed on Mar. 16, 2001, and a continuation-in-part of application No. 09/528,120, filed on Mar. 17, 2000, now Pat. No. 6,509,514.

(51) Int. Cl.
*G01N 33/00* (2006.01)
*A01K 67/27* (2006.01)
*A01K 67/00* (2006.01)
*A01K 67/33* (2006.01)

(52) U.S. Cl. .................. 800/3; 800/8; 800/13; 800/18
(58) Field of Classification Search .............. 800/3, 800/18, 21, 25, 13, 8
See application file for complete search history.

(56) References Cited

U.S. PATENT DOCUMENTS

| | | | |
|---|---|---|---|
| 5,652,373 A | 7/1997 | Reisner | |
| 5,698,767 A | 12/1997 | Wilson et al. | |
| 5,709,843 A | 1/1998 | Reisner | |
| 5,804,160 A | 9/1998 | Reisner | |
| 5,849,288 A | 12/1998 | Reisner | |
| 5,849,987 A | 12/1998 | Reisner | |
| 5,858,328 A | 1/1999 | Reisner | |
| 5,866,757 A | 2/1999 | Reisner | |
| 5,980,886 A | 11/1999 | Kay et al. | |
| 5,994,617 A | 11/1999 | Dick et al. | |
| 6,034,297 A | 3/2000 | Vierling | |
| 6,660,905 B1 | 12/2003 | Kay et al. | |
| 6,864,402 B1 | 3/2005 | Rogler et al. | |
| 2004/0148646 A1 | 7/2004 | Kay et al. | |
| 2004/0158885 A1 | 8/2004 | Rogler et al. | |

FOREIGN PATENT DOCUMENTS

| | | |
|---|---|---|
| EP | 0 438 053 A1 | 7/1991 |
| WO | WO 93/07165 | 4/1993 |
| WO | WO 94/02601 | 2/1994 |
| WO | WO 94/27556 | 12/1994 |
| WO | WO 96/18419 | 6/1996 |
| WO | WO 98/42824 | 10/1998 |
| WO | WO 99/16307 | 4/1999 |
| WO | WO 99/46598 | 9/1999 |
| WO | WO 00/17338 | 3/2000 |
| WO | WO 01/32009 | 5/2001 |

OTHER PUBLICATIONS

Bumgardner et al. Transplantation, 65(10): 53-61 (1998).*
Bronowicki et al. (1998) "Hepatitis C Virus Persistence in Human Hematopoietic Cells Injected Into SCID Mice" *Hepatol.* 28:211-218.
Choo et al. (1989) "Isolation of a cDNA clone derived from a blood-borne non-A, non-B viral hepatitis genome" *Science* 244:359-362.
Crabb (2001) "Hard-Won Advances Spark Excitement About Hepatitis C" *Science* 294:506-507.
Cramp et al. (1999) "Hepatitis C virus (HCV) specific immune responses in anti-HCV positive patients without hepatitis C viraemia" *Gut* 44:424-429.
Dandri et al. (2001) "Repopulation of Mouse Liver With Human Hepatocytes and In Vivo Infection With Hepatitis B Virus" *Hepatol.* 33(4) 981-988.
Dhillon et al. (1995) "Pathology of Hepatitis C Virus Infection" *Histopathol.* 26:297-309.
Fausto, N. (2001) "A Mouse Model For Hepatitis C Virus Infection?" *Nat. Med.* 7(8) 890-891.
Fournier et al. (1998) "In Vitro Infection of Adult Normal Human Hepatocytes in Primary Culture by Hepatitis C Virus" *J. Gen. Virol.* 79(Pt 10):2367-2374.
Galun et al. (1995) "Hepatitis C Virus Viremia in SCID®BNX Mouse Chimera" *J. Infect. Dis.* 172:25-30.
Heckel et al. (1990) "Neonatal Bleeding In Transgenic Mice Expressing Urokinase-Type Plasminogen Activator" *Cell* 62:447-456.
Houdebine et al. (1994) "Production of pharmaceutical proteins from transgenic animals" *J. Biotechnol.* 34:269-287.

(Continued)

*Primary Examiner*—Deborah Crouch
*Assistant Examiner*—Thaian N. Ton
(74) *Attorney, Agent, or Firm*—Carol L. Francis; Edward J. Baba; Bozicevic, Field & Francis LLP

(57) ABSTRACT

The present invention features a non-human animal model that is susceptible to infection by human hepatotrophic pathogens, particularly human hepatitis C virus (HCV). The model is based on a non-human, immunocompromised transgenic animal having a human-mouse chimeric liver, where the transgene provides for expression of a urokinase-type plasminogen activator in the liver. The invention also features methods for identifying candidate therapeutic agents, e.g., agents having antiviral activity against HCV infection. The animals of the invention are also useful in assessing toxicity of various agents, as well as the activity of agents in decreasing blood lipids.

8 Claims, 6 Drawing Sheets

OTHER PUBLICATIONS

Houghton, M. (1996) "Hepatitis C Viruses" in: Field's Virology, 3rd Edition, Chapter 32, 1035-1036.

Ito et al. (1995) "Cultivation of Hepatitis C Virus in Primary Hepatocyte Culture from Patients with Chronic Hepatitis C Results in Release of High Titre Infectious Virus" *J. Gen Virol.* 77:1043.

Kappel et al. (1992) "Regulating gene expression in transgenic animals" *Curr. Biol.* 3:548-553.

Lampertico et al. (1991) "Development and Application of an In Vitro Model for Screening Anti-hepatitis B Virus Therapeutics" *Hepatol.* 13:422-426.

Sureau, C. (1993) "In Vitro Culture Systems for Hepatitis B and Delta Viruses" *Arch. Virol.* 8:3-14.

Toth et al. (1996) "Two Distinct apolipoprotein B alleles in mice generated by a single 'in-out' targeting" *Gene* 178(1):161-168.

Vrancken-Peeters et al. (1997) "Expansion of Donor Hepatocytes After Recombinant Adenovirus-Induced Liver Regeneration in Mice" *Hepatol.* 25(4):884-888.

Wall, R.J. (1996) "Transgenic Livestock: Progress and Prospects for the Future" *Theriogenology* 45:57-68.

Weglarz et al. (2000) "Hepatocyte Transplantation into Diseased Mouse Liver" *Am. J. Pathol.* 157(6):1963-1974.

Xie et al. (1998) "Transmission of Hepatitis C Virus Infection to Tree Shrews" *Virology* 244:513-520.

Lerat et al. (1998) "Hepatitis C Virus Transgenic Mice as Model for HCV Associated Liver Disease", *Hepatology* 28(4Pt2):498A.

Lieber et al. (1995) "A Modified Urokinase Plasminogen Activator Induces Liver Regeneration Without Bleeding" *Hum. Gene Ther.* 6:1029-1037.

Lieber et al. (1995) "Adenovirus-mediated Urokinase Gene Transfer Induces Liver Regeneration and Allows for Efficient Retrovirus Transduction of Hepatocytes in vivo" *Proc. Natl. Acad. Sci. Genet.* 92(20): 6210-6214.

Liu et al. (1993) "Molecular Cloning and Characterization of cDNA Encoding Mouse Hepatocyte Growth Factor" *Biochim. Biophys. Acta* 1216:299-303.

McBurney et al. (1994) "Murine PGK-1 Promoter Drives Widespread But Not Uniform Expression in Transgenic Mice" *Devel. Dynamics* 200(4): 278-298.

Mercer et al. (2001) "Hepatitis C Virus replication in Mice With Chimeric Human Livers" *Nat. Med.* 7(8): 1-7.

Mullins et al. (1996) "Transgenesis in Non-Murine Species" *J. Clin. Invest. Supp.* 98(11):S37-S40.

Nicolet et al. (1998) "Caractérisation de la Régénération Hépatique Chez la Souris Transgénique Albumine-Urokinase" *Chirurgie* 123(1):47-53.

Oldach, D.W. (1998) "Murine Model for Hepatitis C Virus Investigations" University of Maryland Balt Prof School, Grant Abstract, 1 page.

Petersen et al. (1998) "Liver Repopulation with Xenogenic Hepatocytes in B and T Cell-deficient Mice Leads to Chronic Hepadnavirus Infection and Clonal Growth of Hepatocellular Carcinoma" *Proc. Nat'l. Acad. Sci. USA* 95:310-315.

Rhim et al. (1994) "Replacement of Diseased Mouse Liver by Hepatic Cell Transplantation" *Science* 263:1149-52.

Rhim et al. (1995) "Complete Reconstitution of Mouse Liver with Xenogenic Hepatocytes" *Proc. Nat'l. Acad. Sci. USA* 92:4942-4946.

Sandgren et al. (1990) "Complete Hepatic Regeneration After Somatic Deletion of an Albumin-Plasminogen Activator Transgene" *Cell* 6:245-256.

Sarbah et al. (2000) "Hepatitis C: an update on the silent epidemic" *J. Clin. Gastroenterol.* 30(2):125-143.

Sells et al. (1987) "Production of Hepatitis B Virus Particles in Hep G2 Cells Transfected With Cloned Hepatitis B Virus DNA" *Proc. Nat'l. Acad. Sci. USA* 84:1005-1009.

Shapiro, C.N. (1995) "Occupational Risk of Infection with Hepatitis B and Hepatitis C Virus" *Surgical Clinics North Amer.* 75(6):1047-1056.

* cited by examiner

FIG. 1
Weeks post Transplant
Alb-uPA(-)   Alb-uPA(+)
FIG. 5
Weeks
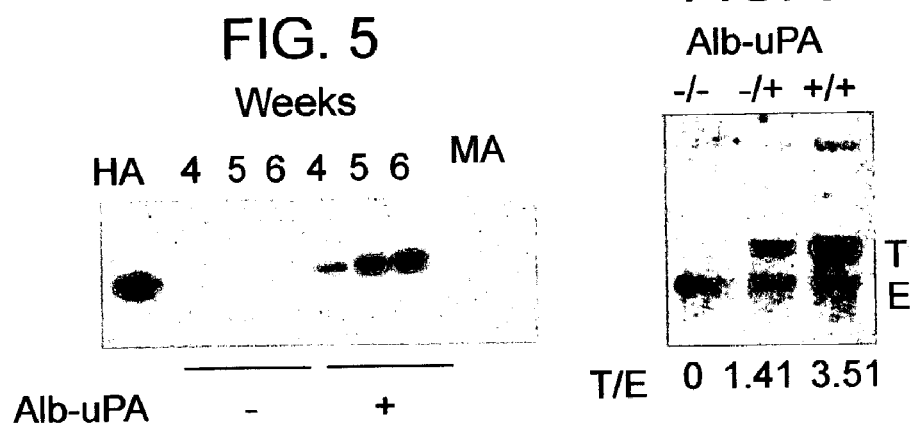
FIG. 6
Alb-uPA
FIG. 7
Weeks Post-Transplant
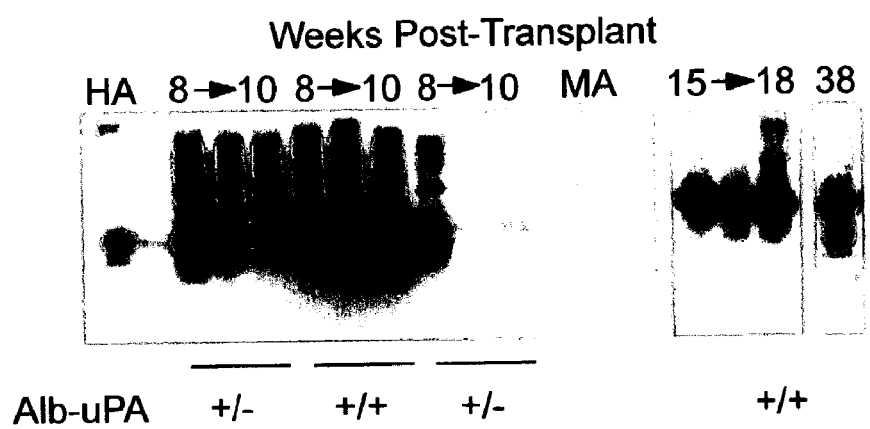

FIG. 11A
FIG. 11B
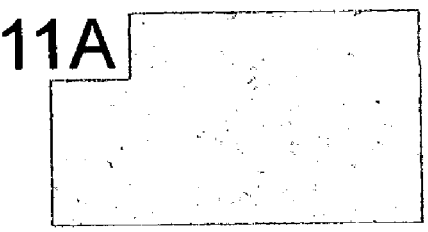
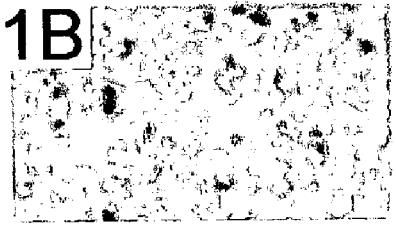
FIG. 12

US 7,161,057 B2

ANIMAL MODEL HAVING A CHIMERIC HUMAN LIVER

CROSS-REFERENCE TO RELATED APPLICATIONS

This application is a continuation-in-part of PCT application Ser. No. PCT/CA01/00350, filed Mar. 16, 2001, and a continuation-in-part of U.S. application Ser. No. 09/528,120, filed Mar. 17, 2000, now U.S. Pat. No. 6,509,514, each of which applications are incorporated herein by reference in entirety.

FIELD OF THE INVENTION

The present invention relates generally to animals useful as a model of infection by a viral pathogen, such as hepatitis virus, as well as in assessment of toxicity and evaluation of therapies for hyperlipidemia.

BACKGROUND OF THE INVENTION

Human liver disease caused by the hepatitis C virus (HCV) has emerged over the past decade as one of the most difficult challenges facing the worldwide medical community. Elucidation of the viral sequence in 1989 (Choo, et al. Science 244, 359–361 (1989)) initiated the era of concerted study of HCV; presently it is estimated that up to 175,000,000 people are infected (Sarbah, et al. Cell 62, 447–456 (1990)). HCV is the most common type of chronic viral hepatitis with an estimated prevalence of 1–2% in developed countries. Chronic HCV hepatitis leads to liver cirrhosis in at least 25% of affected patients and after development of cirrhosis it is estimated that hepatocellular carcinoma develops in 1–4% of patients each year. In North America HCV is currently the most common indication for liver transplantation.

Currently antiviral therapy with combination interferon and ribavirin is effective in selected patients, but many either fail to respond or tolerate therapy poorly, underscoring a need for improvement. Sustained response rates for interferon monotherapy range from 20–25%, while combination therapy with interferon and ribavirin has shown sustained response rates of up to 40%. Although newer antiviral drugs targeting different parts of the viral genome are under development, progress has been severely hampered by the lack of a robust cost-effective animal model of HCV. The only natural hosts for HCV are humans and chimpanzees, neither of which is suitable for large scale antiviral testing.

The lack of a reproducible small animal model for HCV infection has further limited the investigation of various immune factors contributing to the disease, as well as vaccine candidates for the immunotherapy of chronic HCV infections. In the case of HCV infection, a number of reports have demonstrated the presence of Th1->Th2 switch and HCV antigens specific CD4+ and CD8+T cells in in vitro studies on T cells isolated from the HCV infected individuals. On the other hand, non-viremic HCV infected patients have been found to stimulate strong Th1 response to multiple HCV antigens even many years after infections, suggesting that control of HCV replication may depend on effective Th1 activation (Cramp et al. *Gut* 44:424–429 (1999)). Resolution of these questions to provide a better understanding of the immune response to HCV, and thus insight as to the development of effective vaccines and therapies, can not be easily reached without a suitable animal model.

Over the past several years, significant advances have been made in the development of animal models for hepatitis B virus. However, despite their similar sounding names, human hepatitis B virus (HBV) and human hepatitis C virus (HCV) are completely different viruses, and thus research regarding HBV infection can not be readily extrapolated to HCV infection. Both viruses are referred to as "hepatitis" viruses primarily because HBV and HCV infect and replicate in the liver. Aside from this, HBV and HCV are no more alike than are HIV and EBV, which each affect the immune system. In fact, HBV and HCV are so different that they are not even member of the same phylogenetic family. HBV is a member of the hepadnavirus family with a genome of double-stranded DNA, whereas HCV is a member of the flavivirus family, which is based on a single positive-stranded RNA genome.

HBV and HCV also differ in their infectivity. HCV is less infectious than an equivalent dose of HBV, as evidenced by the differences in acquisition rates in hospital personnel after needlestick injuries. HBV infections occur in 2–40% of HBV-contaminated needlestick events, while HCV infections occur in only 3–10% of HCV-contaminated needlestick events. These observations suggest that HCV is about three to four times less infectious than HBV (Shapiro *Surgical Clin North Amer.* 75(6):1047–56 (1995)).

HBV and HCV differ greatly in their requirements for replication as well as in the viral load during infection. HBV is capable of replicating in less differentiated systems (e.g., HepG2 cells, Sells et al. *Proc. Natl. Acad. Sci.* USA 84:1005 (1987)). In contrast, HCV replication may depend upon the presence of nontransformed hepatocytes (see, e.g., Ito et al. *J. Gen. Virol.* 77:1043 (1995)). The viral titers of patients infected with HCV are generally lower than those of HBV-infected patients. Patients infected with HBV have levels ranging from $10^5$ to $10^9$ particles per mL, compared to $10^2$ to $10^7$ particles per mL in HCV infections. These differences in viral titer may be due at least in part to the relative clearance rates of viral particles. In addition, the number of viral copies per cell is also very low in HCV infection (e.g., generally less than 20 copies per cell (Dhillon et al. *Histopathology* 26:297–309 (1995)). This combination of low viral titers and low number of viral copies per cell means that a significant number of human hepatocytes must be infected and producing virus for the infection to even be detected within serum.

The limited host range of human HBV and human HCV has proved problematic in the development of in vitro and in vivo models of infection. Humans and chimpanzees are the only animals susceptible to human HBV infection; human, chimpanzees, and tree shrews are susceptible for infection with human HCV (Xie et al. *Virology* 244:513–20 (1998), reporting transient infection of tree shrews with HCV). Human HBV will infect isolated human liver cells in culture (see, e.g., Sureau *Arch. Virol.* 8:3–14 (1993); Lampertico et al. *Hepatology* 13;422–6 (1991)). HCV has been reported to infect primary cultures of human hepatocytes; however, the cells do not support the production of progeny virions (Fournier et al. *J Gen Virol* 79(Pt 10):2367–74 (1998)). The development of a satisfactory in vivo model is required in order to provide a more clinically relevant means for assaying candidate therapeutic agents.

The extremely narrow host range of HBV and HCV has made it very difficult to develop animal models. Current animal models of HBV and HCV either do not involve the normal course of infection, require the use of previously infected human liver cells, or both (see, e.g., U.S. Pat. Nos. 5,709,843; 5,652,373; 5,804,160; 5,849,288; 5,858,328; and 5,866,757; describing a chimeric mouse model for HBV infection by transplanting HBV-infected human liver cells under the mouse kidney capsule; WO 99/16307 and Galun et al. *J. Infect. Dis.* 172:25–30 (1995), describing transplantation of HCV-infected human hepatocytes into liver of immunodeficient mice; Bronowicki et al. *Hepatology* 28:211–8 (1998), describing intraperitoneal injection of HCV-infected hematopoietic cells into SCID mice; and Lerta et al. *Hepatology* 28(4Pt2):498A (1998), describing mice transgenic for the HCV genome). Infection by human HBV is fairly well mimicked by infection of woodchucks with woodchuck hepatitis virus (WHV) and by infection of Peking ducks with duck hepatitis virus (DHV). WHV-infected woodchucks and DHV-infected ducks have been successfully used to identify drugs effective against human HBV infection of humans. However, no analogous animal model of infection has been identified for human HCV.

In the absence of a practical non-human host, the most desirable animal model would be a chimeric animal model that allowed for infection of human liver cells through the normal route of infection, preferably a mouse model susceptible to viral infection through intravenous inoculation and that could support chronic infection. Unfortunately, the development of mice having chimeric livers with human hepatocytes susceptible to HBV or HCV infection, and sustaining viral replication and virion production at clinically relevant, sustainable levels has proven no simple matter. The field of xenogeneic liver transplantation has moved very slowly and met with many obstacles.

In order to study neonatal bleeding disorders and hypofibrinogenemia, a mouse transgenic for an albumin-urokinase-type plasminogen activator construct (Alb-uPA) was developed (Heckel et al. *Cell* 62:447–56 (1990); Sandgren et al. *Cell* 66:245–56 (1991)). The Alb-uPA transgene includes a murine urokinase gene under the control of the albumin promoter, resulting in the targeting of urokinase production to the liver and producing a profoundly hypofibrinogenemic state. This transgene was also found to be associated with accelerated hepatocyte death. Later work with this transgenic animal demonstrated that individual hepatocytes that spontaneously deleted the transgene acquired a significant survival and replicative advantage, resulting in repopulation of the liver with these nontransgenic cells Sandgren et al., (1991), supra). The Alb-uPA transgenic mouse has proved amenable to transplantation with liver cells from non-transgenic mice (Rhim et al. *Science* 263:1149–52 (1994)). The Alb-uPA transgenic mouse was also successfully used to produce mice having chimeric livers with rat hepatocytes (Rhim et al. *Proc. Natl. Acad. Sci. USA* 92:4942–6 (1995)) or woodchuck hepatocytes (Petersen et al. *Proc. Natl. Acad. Sci. USA* 95:310–5 (1998).

However, these developments were still a long step away from the development of an animal model susceptible to HCV infection. Production of mouse having a xenogeneic transplant from another member of the Rodentia family is not nearly as difficult or unexpected as production of a mouse having a xenogeneic transplant from an animal of a different family, e.g., a human, much less would one expect that a high degree of chimerism could be accomplished, or that such chimeric animals might support HCV infection. For example, hepatocyte growth factor (HGF) is the most potent stimulus of hepatocyte regeneration in vivo; in comparing sequence data, mouse HGF was shown to have 98.5% amino acid sequence homology with rat HGF, and only 90.9% with human HGF (Liu et al. *Biochim et Biophys Acta* 1216;:299–303 (1993)). There were no guarantees of success.

There is a need in the field for a human-mouse liver chimera susceptible to chronic infection with HCV and with viral production at clinically relevant levels. The present invention addresses this problem.

SUMMARY OF THE INVENTION

The present invention features a non-human animal model that is susceptible to infection by human hepatotrophic pathogens, particularly human hepatitis C virus (HCV). The model is based on a non-human, immunocompromised transgenic animal having a human-mouse chimeric liver, where the transgene provides for expression of a urokinase-type plasminogen activator in the liver. The invention also features methods for identifying candidate therapeutic agents, e.g., agents having antiviral activity against HCV infection. The animals of the invention are also useful in assessing toxicity of various agents, as well as the activity of agents in decreasing blood lipids.

In one aspect the invention provides a non-human animal model that is susceptible to infection by human HCV via the normal route of infection.

In another aspect the invention provides a non-human animal model is useful in assessing toxicity of an agent.

In another aspect the invention provides a non-human animal model is useful in identifying agents that decrease blood lipids.

An advantage of the invention is that the animal model provides the first instance of an animal that is susceptible to infection by HCV via the normal route of infection, and further that can become chronically, consistently, and stably infected at viral titers that can be equated to viral titers in HCV-infected humans.

Still another advantage of the invention is that production of the animal model does not require obtaining or handling HCV-infected cells. Thus the invention avoids the need to obtain hepatocytes from HCV-infected human donors or to culture and infect human hepatocytes in vitro.

Another advantage of the invention is that provides for methods for assessing toxicity and drug efficacy in an in vivo setting, rather than liver cells in vitro.

These and other objects, advantages, and features of the invention will become apparent to those persons skilled in the art upon reading the details of the animal model and methods of its use as more fully described below.

BRIEF DESCRIPTION OF THE DRAWINGS

FIG. 1 is a Western blot of human albumin (HA) production in recipient serum samples over time in animals carrying or not carrying the Alb-uPA transgene FIG. 2A is a low power H&E section of control mouse liver taken from a nontransplanted homozygous Alb-uPA liver, showing uniform cellular architecture. FIG. 2B is a low power H&E section from a transplanted homozygous mouse, showing a large nodule of tissue compressing surrounding host-derived liver parenchyma. FIGS. 2C and 2D show control sections of mouse and human liver respectively, both immunostained with an anti-human hepatocyte antibody, demonstrating the immunohistochemical procedure clearly stains human cells, but not murine cells. FIG. 2E is a high power H&E stained section of transplanted homozygote liver, showing a nodule of healthy hepatocytes compressing surrounding tissue. FIG. 2F is a consecutive section immunostained for human hepatocyte antigen, showing the darker nodule to be comprised of human cells, with the surrounding parenchyma being of murine origin.

FIG. 5 is a photograph of a Western blot showing detection of human albumin (HA) produced from human hepatocytes in chimeric livers (samples represent individual mice). Wild-type (−); transgenic (+) recipients. HA—human albumin standard; MS—nontransplanted mouse serum (negative control).

FIG. 6 is a photograph of a Southern blot for determination of Alb-uPA zygosity from genomic DNA; a T/E ratio of ~2 is characteristic of hemizygous mice, while homozygotes have a ratio of ~4.

FIG. 7 is a photograph of a Western blot showing long-term HA production in transplant recipients hemizygous (+/−) or homozygous (+/+) for the Alb-uPA transgene. HA—human albumin standard; MS—nontransplanted mouse serum (negative control).

FIG. 10B is a photograph of a gel of a dilution series analysis of selected animals using the thermostable rTth reverse transcriptase RNA PCR protocol. Letter and number designations are the same as in FIG. 10A.

FIGS. 11A and 11B are photographs showing immuno-histochemical analysis of control (FIG. 11A) and HCV infected (FIG. 11B) liver sections using ant anti-HCV antibody.

FIG. 12 is a photograph of a Western blot to detect Apo B100 in serum of a chimeric Alb/uPA, transplanted animal (lane 2). Human serum (lane 1) and serum from Alb/uPA a non-transplanted animal (lane 3) served as positive and negative controls, respectively.

DETAILED DESCRIPTION OF PREFERRED EMBODIMENTS

Figure 2A:
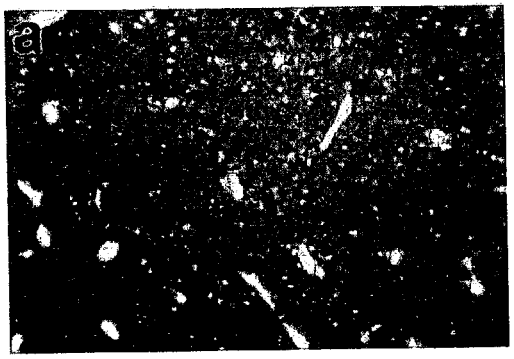
FIGS. 2A–2F are photographs of histochemical analysis of human chimerism in mouse livers.
Figure 2B:
Figure 2C:
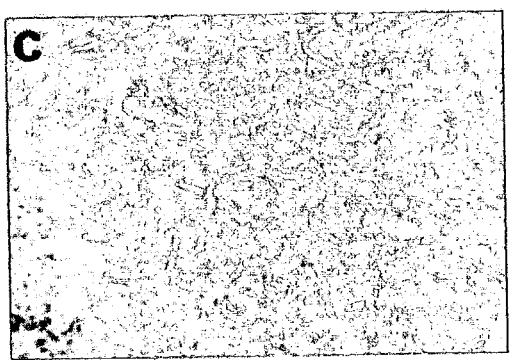
Figure 2D:
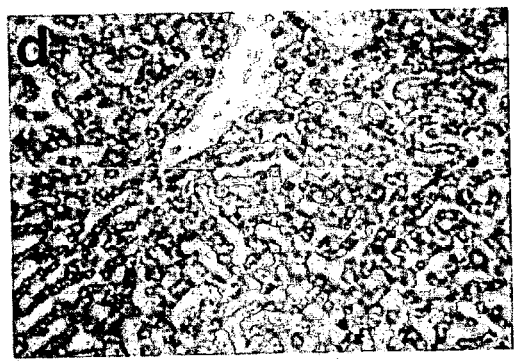
Figure 2E:
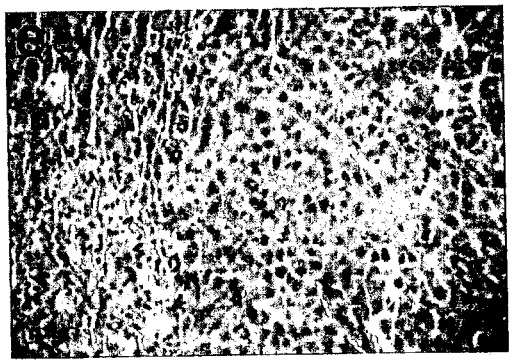
Figure 2F:

Before the present invention is described, it is to be understood that this invention is not limited to particular methodology, protocols, cell lines, animal species or genera, constructs, and reagents described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a liver cell" includes a plurality of such liver cells and reference to "the non-human animal" includes reference to one or more non-human animals and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

"Chimeric" as used herein (e.g., "chimeric animal" or "chimeric liver") is meant to describe an organ or animal comprising xenogeneic tissues or cells. Of particular interest is a chimeric animal, wherein the animal is chimeric due to the presence of human hepatocytes engrafted in the animal's liver.

By "immunocompromised" is meant that the animal can not mount a complete or significant immune response against the xenogeneic tissue or cells, e.g., any immune response of the host animal is such that it is ineffective in rejection of the transplanted cells.

The term "transgene" is used herein to describe genetic material which has been or is about to be artificially inserted into the genome of a mammalian, particularly a mammalian cell of a living animal.

By "transgenic animal" is meant a non-human animal, usually a mammal, having a non-endogenous (i.e., heterologous) nucleic acid sequence present as an extrachromosomal element in a portion of its cells or stably integrated into its germ line DNA (i.e., in the genomic sequence of most or all of its cells). Heterologous nucleic acid is introduced into the germ line of such transgenic animals by genetic manipulation of, for example, embryos or embryonic stem cells of the host animal according to methods well known in the art. A "transgene" is meant to refer to such heterologous nucleic acid, e.g., heterologous nucleic acid in the form of an expression construct (e.g., for the production of a "knock-in" transgenic animal) or a heterologous nucleic acid that upon insertion within or adjacent a target gene results in a decrease in target gene expression (e.g., for production of a "knock-out" transgenic animal).

A "knock-out" of a gene means an alteration in the sequence of the gene that results in a decrease of function of the target gene, preferably such that target gene expression is undetectable or insignificant. Transgenic knock-out animals can be comprise a heterozygous knock-out of a target gene, or a homozygous knock-out of a target gene. "Knock-outs" as used herein also include conditional knock-outs, where alteration of the target gene can occur upon, for example, exposure of the animal to a substance that promotes target gene alteration, introduction of an enzyme that promotes recombination at the target gene site (e.g., Cre in the Cre-lox system), or other method for directing the target gene alteration postnatally.

A "knock-in" of a target gene means an alteration in a host cell genome that results in altered expression (e.g., increased (including ectopic) or decreased expression) of a target gene, e.g., by introduction of an additional copy of the target gene, or by operatively inserting a regulatory sequence that provides for enhanced expression of an endogenous copy of the target gene. "Knock-in" transgenics can comprise a heterozygous knock-in of the target gene or a homozygous knock-in of a target gene. "Knock-ins" also encompass conditional knock-ins.

By "operably linked" is meant that a DNA sequence and a regulatory sequence(s) are connected in such a way as to permit gene expression when the appropriate molecules (e.g., transcriptional activator proteins) are bound to the regulatory sequence(s).

By "operatively inserted" is meant that a nucleotide sequence of interest is positioned adjacent a nucleotide sequence that directs transcription and translation of the introduced nucleotide sequence of interest.

The term "therapeutic agent" as used herein refers to any molecule, e.g., protein or small molecule, pharmaceutical compound, antibody, antisense molecule, ribozyme, and the like, useful in the treatment of a disease or condition, e.g., a liver condition, including, but not necessarily limited to infection by HCV. For example, therapeutic agents of the invention include molecules that inhibit, ameliorate, or relieve symptoms associated with viral infection, and in particular HCV.

The term "unit dosage form" as used herein refers to physically discrete units suitable as unitary dosages for subjects (e.g., animals, usually humans), each unit containing a predetermined quantity of agent(s) in an amount sufficient to produce the desired effect in association with a pharmaceutically acceptable diluent, carrier or vehicle. The specifications for the novel unit dosage forms of the present invention will depend on a variety of factors including, but not necessarily limited to, the particular agent employed and the effect to be achieved, and the pharmacodynamics associated with each compound in the host.

The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, particularly a human, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease.

Overview

The present invention is based on the development of a murine animal model having a chimeric liver with human hepatocytes, and which is susceptible to infection by human hepatitis C virus (HCV). The murine animal model generally involves transplantation of human hepatocytes into the liver of a transgenic mouse at an appropriate stage of the host's development, preferably shortly after birth of the host. Without being held to theory, success in the development of the model is due at least in part to the following: 1) use of a host having an immunodeficient background, thus avoiding immune destruction of introduced xenogenic (human) cells; 2) the use of a transgenic animal that contains a transgene for urokinase linked to an albumin promoter, which is present in the homozygous state, thereby providing an ongoing potent stimulus to hepatocyte growth and cellular division; and, 3) introduction of viable human hepatocytes into the host animal at an appropriate time in the hepatocyte life cycle and at an early stage of the host animal's development to provide for long-term survival of either large numbers and/or a high percentage of human cells in the host.

To the best of the inventors' knowledge, the present invention for the first time provides a non-primate host for use as a model of HCV infection that can be infected through the normal route of infection (e.g., by intravenous or intraperitoneal inoculation). This aspect of the invention is particularly important for use in the development of antiviral agents. Furthermore, the animal model of the invention does not require the use of pre-infected human hepatocytes, thus avoiding the handling of infected tissue isolated from human donors or infecting the human hepatocytes in vitro prior to implantation.

Accordingly the invention features a chimeric animal as described above, as well as a method of producing a chimeric animal by transplanting human hepatocytes into the liver of an immunocompromised, albumin linked urokinase transgene-bearing animal. In addition the invention features methods of using the chimeric animal model described herein, including methods of identifying agents for treatment of infections by a hepatotrophic microbial pathogen.

In other aspects the invention features methods of using the non-human animal model of the invention in assessing toxicity and evaluating drugs in modulation of levels of blood lipids.

The invention will now be described in more detail.

Host Animals

The host animal is generally a non-human, immunocompromised mammal having an increased production in the liver of urokinase-type plasminogen activator (uPA) and in which human hepatocytes can be engrafted and maintained. Exemplary non-human animals upon which the animal model of the invention can be based include, but are not necessarily limited to, mice, rats, guinea pigs, hamsters, sheep, pigs, primates, and the like. In one embodiment, the host animal is of the genus Rodentia, preferably a mouse. In a preferred embodiment, the host animal is an immunocompromised mouse, preferably an immunocompromised mouse transgenic for urokinase-type plasminogen activator (uPA), more preferably an immunocompromised mouse comprising a transgene that provides for liver-specific production of uPA (e.g., an Alb-uPA transgene, see, e.g., Heckel et al *Cell* 62:447 (1990)). Mice suitable for use in the present invention can be produced from any of a variety of background strains including, but not necessarily limited to, the strains C.B-17, C3H, BALB/c, C57131/6, AKR, BA, B10, 129, etc. The host animal maybe either male or female.

Immunocompromised Background

As noted above, the host animal is preferably immunocompromised. Immunocompromised mammalian hosts suitable for implantation and having the desired immune incapacity are available. Alternatively, though less preferred, immunocompromised animals can be generated from immunocompetent animals by, for example, administration of one or more compounds (e.g., cyclosporin) and other methods well known in the art. In general, the immunocompromised host can not mount a complete immune response against the xenogeneic tissue or cells. Of particular interest are animals that are immunocompromised due to a genetic defect that results in an inability to undergo germline DNA rearrangement at the loci encoding immunoglobulins and T-cell antigen receptors. Also of interest are immunocompromised animals that have one or more genetic defects that leads to significantly decreased numbers of or no detectable functional T cells, B cells, and natural killer (NK) cells relative to normal.

Of particular interest are mice that have a homozygous mutation at the scid locus (scid/scid). The scid mutation is associated with a deficiency in DNA-dependent protein kinase catalytic subunit and prevents VDJ recombination in immunoglobulin and T-cell receptor genes. Animals homozygous for the scid mutation lack functionally recombined immunoglobulin and T-cell receptor genes and thus are deficient in both T and B cell lineages. The scid/scid mutation is available or may be bred into a number of different genetic backgrounds, e.g., CB.17, ICR (outbred), C3H, BALB/c, C57B1/6, AKR, BA, B10, 129, etc. The invention can also take advantage of animals having the beige mutation (bg), which is associated with a natural killer (NK) cell deficiency. In one embodiment, mice are produced having both the scid mutation and the bg beige mutation, resulting in an animal that does not mount an effective immune response to allogeneic or xenogeneic cells or tissues introduced to the organisms.

Other exemplary immunocompromised host that are presently available include transgenic mice genetically engineered to lack the recombinase function associated with RAG-1 and/or RAG-2 (e.g., commercially available TIM™ RAG-2 transgenic), to lack Class I and/or Class II MHC antigens (e.g., the commercially available C1D and C2D transgenic strains), or to lack expression of the Bc1–2 proto-oncogene. Other mice that may be useful as recipients are NOD scid/scid; SGB scid/scid, bh/bh; CB. 17 scid/hr; NIH-3 bg/nu/xid and META nu/nu. Transgenic mice, rats and pigs are available which lack functional B cells and T cells due to a homozygous disruption in the CD3F-gene. Immunocompromised rats include HsdHan:RNU-rnu; HsdHan:RNU-rnu/+; HsdHan:NZNU-rnu; HsdHan:NZNU-rnu/+; LEW/HanHsd-rnu; LEW/HanHsd-rnu/+; WAG/HanHsd-rnu and WAG/HanHsd-rnu/+.

Transgenic Expression of Urokinase

As discussed above, the chimeric animal of the invention is also a "knock-in" transgenic for expression of urokinase-type plasminogen activator (uPA). In one embodiment, the transgene is the Alb-uPA transgene, which comprises a murine albumin enhancer/promoter, the murine uPA gene coding region, and the 3' untranslated and flanking sequences of the growth hormone gene (Heckel et al. *Cell* 62:447–56 (1990); Sandgren et al. *Cell* 66:245–56 (1991)). Preferably the animal is homozygous, rather than heterozygous, for the urokinase-type plasminogen activator transgene. The Alb-uPA transgene results in a lethal insult to hepatocytes that carry it, and also results in a high local (intrahepatic) concentration of urokinase, which in turn processes hepatocyte growth factor to its active form within the liver. Without being held to theory, viable allogeneic or xenogeneic cells introduced at an appropriate time in the development of an Alb-uPA transgenic animal are stimulated to replicate in this environment. The donor cells thus grow to "replace" the endogenous hepatocytes that die as a result of the lethal insult of the transgene.

Isolation of Human Hepatocytes and other Cells Suitable for Transplantation

Human hepatocytes for transplantation into the host animals are isolated from human liver tissue by any convenient method known in the art. In general, the human hepatocytes may be fresh tissue (e.g., obtained within hours of death), or freshly frozen tissue (e.g., fresh tissue frozen and maintained at or below about 0° C.). Ideally, the cells used are recently isolated (i.e., within 2 to 4 hours) from freshly obtained human liver tissue. Human hepatocytes that are placed in a defined cryopreservation media may be stored for long periods of time (e.g., in liquid nitrogen) and thawed as required, thus permitting the development of banks of stored hepatocytes. In general, it is usually important that the isolation procedure and handling and storage protocol serve to minimize warm ischemia following cessation of blood flow to the liver (e.g., generally less than about 30 min to 60 min, preferably less than about 20 min to about 40 min) and to minimize cold ischemia that may result from storage (e.g., generally less than about 12 hr, usually less than about 1 hr to 2 hrs). In one embodiment, the human tissue is normal, e.g., having no detectable pathogens, normal in morphology and histology, and essentially disease-free). Usually the period of warm ischemia exposure is not more than about 20–50 minutes.

The liver tissue can be dissociated mechanically or enzymatically to provide a suspension of single cells, or fragments of intact human hepatic tissue may be used. In a preferred embodiment, the hepatocytes are isolated from donor tissue by routine collagenase perfusion (Ryan et al. *Meth. Cell Biol.* 13:29 (1976)) followed by low-speed centrifugation. Hepatocytes can then be purified by filtering through a stainless steel mesh (e.g., 100 µm), followed by density-gradient centrifugation. Alternatively, other methods for enriching for hepatocytes can be used, e.g., fluorescence activated cell sorting, panning, magnetic bead separation, elutriation within a centrifugal field, etc. The final suspension used for implantation generally comprises at least about 50–75% hepatocytes, usually at least about 80–99% hepatocytes, generally with viability by trypan blue exclusion of 80–99%, In another embodiment, the cells to be transplanted are human stem cells or hepatocyte precursor cells which, following transplantation into the host animal's liver, develop or differentiate into human hepatocytes susceptible to HCV infection. In one specific embodiment, the human stem cells are obtained from human blood cord cells. Human blood cord cells are not only a source for stem cell reconstitution of hepatocytes, but also for reconstitution of the immune system (see, e.g., Verstegen et al. Blood. 91(6): 1966–76 (1998)).

Transplantation of Human Hepatocytes or other Suitable Cells into Hosts

The timing of the introduction of the donor hepatocytes into the transgenic, immunocompromised host may be important to the production of a chimeric liver populated with a number of human hepatocytes sufficient to render the chimeric liver susceptible to infection by a hepatotrophic pathogen and to support replication of the pathogen. This may be particularly true where the hepatotrophic pathogen exhibits low infectivity and/or low replication rates (e.g., HCV). Where the animal is murine (e.g., a mouse), the host is ideally less than 10 days to 2 weeks in age, and optimally about 7 to 10 days old, or less than or about one week (i.e., less than or about 5 to 7 days old or younger), at the time of transplantation. In general, the transplantation is preferably carried out between about 8–10 days and 15 days of age. The window for transplant can be widened to about 7–18 days of age to gain flexibility while maintaining good results. Without being held to theory, the timing of transplantation indicated herein is a compromise between excess technical mortality associated with very early transplantation (i.e., due to the small size of the animals) and the time for maximal replicative stimulus (e.g., the number of cell divisions in the recipient liver that occur before transplant may influence the success and extent of engraftment of the donor human cells). Furthermore, timing of transplantation is also important since the stimulus for liver cell repopulation provided by the transgene diminishes with time, and is generally depleted after the recipient is more than about 6 weeks old (Rhim et al. (1994) *Science* 263:1149–52; about 10–12 weeks for homozygotes).

The human hepatocytes (or other suitable cell, e.g., hepatocyte precursor or stem cell) can be transplanted using any suitable method known in the art. Preferably, the human hepatocytes are injected intrasplenically, e.g., into the inferior splenic pole.

Successful engraftment can be monitored by conventional methods, e.g., by examining the levels of human liver-specific proteins in the host serum, e.g., human serum albumin (HA), or human alpha-1 antitrypsin. The chimeric host can be used for experimentation (e.g., for infection with a hepatotrophic pathogen, to screen candidate agents, etc.) when suitable. Where the animal is to be infected with a hepatotrophic agent of relative low infectivity and/or low replicative capacity, the chimeric animal can be inoculated within about four to six weeks post-transplant, generally at about six weeks post-transplant, and may be as early as three weeks post-transplant.

In general, the animal host develops human chimerism within its liver such that the percentage of liver cells that are human liver cells are from at least about 20% to 50%, generally about 40% to 60% or more, and may be optimized to 90% or more. The chimeric animal can be maintained with functional transplanted hepatocytes for at least several weeks, generally at least about 5 weeks, more usually at least about 12 weeks to 24 weeks, up to 8 months or more, and may be up to the lifespan of the host. Chimeric animals can be infected with a hepatotrophic pathogen (e.g., HCV), particularly a hepatotrophic pathogen having a host range limited to primates, particularly humans. Depending upon the nature of the pathogen, chronically infected chimeric hosts can be maintained for a period of weeks to months. For example, where the hepatotrophic pathogen is HCV, the chimeric animal can become chronically infected with HCV (e.g., chronically infected) and maintain an active HCV infection for a period of at least about 5 weeks, generally at least about 14 weeks to about 20 weeks or more, up to about 35 weeks or more, and may be for the lifespan of the host.

The viral load of the infected host can be established such that it is similar to the viral load of an infected human. For example, where the pathogen is HCV, the host animal can support infection at a level of from about $10^3$ or about $10^4$ to about $10^6$ viral particles/ml serum, generally from about $10^3$ to about $10^7$ viral particles/ml serum.

The viral load of the infected host over time is substantially consistent, chronic, and stable, e.g., the number of viral particles that can be isolated from the infected. untreated host's serum does not radically fluctuate between weekly sampling periods, e.g., an HCV-infected host of the invention that contains a high number of HCV viral particles per mL of serum at a first sampling time is positive for HCV infection at subsequent sampling times and generally has the same or similar high level of HCV particles per mL of serum, once stable infection is established in the host, generally within about 2 to 4 weeks post-infection. In general, the viral load of the infected host does not fluctuate radically and so allows assessment of the effect of a candidate antiviral agent, e.g., the viral titer is chronic and reasonably consistent.

Screening Assays

The chimeric animal of the invention can be used in a variety of other screening assays. For example, any of a variety of candidate agents suspected of causing or contributing to hepatic disease, as well as the appropriate antagonists and blocking therapeutic agents, can be screened by administration to the chimeric animal and assessing the effect of these agents upon function of the engrafted human cells.

In one embodiment of particular interest, the animal model of the invention can be used to identify candidate agents that, for example, inhibit or prevent infection by, replication of, or disease symptoms caused by a hepatotrophic pathogen (e.g., bacteria, virus, parasite, especially a hepatotrophic virus such as HCV). Although the examples provided herein generally involve the use of chimeric murine hosts with a single hepatotrophic pathogen, the invention can also be used to identify a single candidate agent or a cocktail of candidate agents having activity against infection by two or more hepatotrophic agents.

"Candidate agents" is meant to include synthetic, naturally occurring, or recombinantly produced molecules (e.g., small molecule; drugs; peptides; antibodies (including antigen-binding antibody fragments, e.g., to provide for passive immunity) or other immunotherapeutic agents; endogenous factors present in eukaryotic or prokaryotic cells (e.g., polypeptides, plant extracts, and the like)); etc.). Of particular interest are screening assays for agents that have a low toxicity for human cells.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including, but not limited to: peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Screening of Candidate Anti-HCV Agents

In one embodiment, the animal model of the invention is used to identify agents that ameliorate symptoms caused by viral hepatitis, and more specifically by HCV infection and/or to more directly affect a pathogenic mechanism of the infecting virus, e.g., inhibit viral infection, decrease viral replication, or otherwise disrupt the cycle of viral propagation. In general, the candidate agent is administered to the animal model of the invention, and the effects of the candidate agent assessed relative to a control (e.g., relative to an uninfected animal, relative to an HCV-infected animal treated with an agent having a known anti-HCV effect (e.g., IL-2α), and the like). For example, the candidate agent can be administered to an HCV-infected animal of the invention, and the viral titer of the treated animal (e.g., as measured by RT-PCR of serum samples) compared to the viral titer of the animal prior to treatment and/or to a control, untreated HCV-infected animal. In general, a detectable and significant decrease in viral titer of an infected animal following treatment with a candidate agent is indicative of antiviral activity of the agent.

The candidate agent can be administered in any manner desired and/or appropriate for delivery of the agent in order to effect a desired result. For example, the candidate agent can be administered by injection (e.g., by injection intravenously, intramuscularly, subcutaneously, or directly into the tissue in which the desired affect is to be achieved), orally, or by any other desirable means. Normally, the in vivo screen will involve a number of animals receiving varying amounts and concentrations of the candidate agent (from no agent to an amount of agent that approaches an upper limit of the amount that can be delivered successfully to the animal), and may include delivery of the agent in different formulations and routes. The agents can be administered singly or can be combined in combinations of two or more, especially where administration of a combination of agents may result in a synergistic effect.

The activity of the candidate agent can be assessed in a variety of ways. For example, where the host animal is infected with a hepatotrophic pathogen (e.g., HCV, etc.), the effect of the agent can be assessed by examining serum samples for the presence of the pathogen (e.g., titer, as in viral titer) or markers associated with the presence of the pathogen (e.g., a pathogen-specific protein or encoding nucleic acid, etc.) Qualitative and quantitative methods for detecting and assessing the presence and severity of viral infection are well known in the art. In one embodiment, the activity of an agent against HCV infection can be assessed by examining serum samples and/or tissue sections for the presence of a virus (e.g., HCV by RT-PCR, etc.). In another embodiment, the activity of an agent against viral infection can be assessed by examining serum samples for the presence of viral nucleic acid (e.g., HCV RNA). For example, HCV RNA can be detected using, for example, reverse transcriptase polymerase chain reaction (RT-PCR), competitive RT-PCR or branched-DNA (bDNA) assay, detection of negative-strand RNA (the replicative intermediate of HCV) by RT-PCR, or sequencing of viral RNA to detect mutation/shift in the viral genome ("quasispecies evolution") with therapy. Alternatively or in addition, the host liver may be biopsied and in situ RT-PCR hybridization performed to demonstrate directly any qualitative or quantitative alterations in the amount of viral particles within tissue sections. Alternatively or in addition, the host can be euthanized and the liver examined histologically for signs of infection and/or toxicity caused by the agent.

Identified Agents

The compounds having the desired pharmacological activity may be administered in a physiologically acceptable carrier to a host for treatment. The therapeutic agents may be administered in a variety of ways, orally, topically, parenterally e.g. subcutaneously, intraperitoneally, intravascularly, by inhalation, etc. Depending upon the manner of introduction, the compounds may be formulated in a variety of ways. The concentration of therapeutically active compound in the formulation may vary from about 0.1–100 wt. %.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying Agents, salts for varying the osmotic pressure or buffers for securing an adequate pH value, and skin penetration enhancers can be used as auxiliary agents.

Vaccine Development

With some modifications, the animal model of the invention can also be used to screen candidate vaccines for their ability to prevent or ameliorate infection by a hepatotrophic pathogen. In general, a "vaccine" is an agent that, following administration, facilitates the host in mounting an immune response against the target pathogen. The humoral, cellular, or humoral/cellular immune response elicited can facilitate inhibition of infection by the pathogen against which the vaccine is developed. Of particular interest in the present invention are prophylactic vaccines that elicit a protective immune response that inhibits infection by and/or intrahepatic replication of a hepatotrophic pathogen, e.g., a microbial, viral, or parasitic pathogen, particularly a viral pathogen, e.g., HCV. Also of interest are therapeutic vaccines which provide protection through provision of passive immunity or rapidly upregulated specific active immunity (e.g., anti-HCV immunoglobulin, and the like).

In this embodiment of the invention, the immune system of the immunocompromised chimeric animal is reconstituted using, for example, stem cells, peripheral blood mononuclear cells (PBMCs), blood cord cells, hematopoietc cells, or other suitable cells of human origin to provide for a human immune system in the animal. Methods for isolating human immune cells and reconstitution of the immune system of an immunocompromised animal, e.g., a mouse with an human immune system are well known in the art (see, e.g., *Nature* 335:256–59; *Proc. Natl. Acad. Sci. USA* 93(25):14720–25). In one embodiment, the human immune cells are obtained from the same donor as the human hepatocytes used in the production of the chimeric liver. In one embodiment, the human immune cells are introduced into the host according to methods well known in the art, e.g., by intraperitoneal injection.

Screening for an effective vaccine is similar to screening methods described above. In short, the candidate vaccine is administered to the chimeric animal prior to inoculation with the hepatotrophic pathogen. The candidate vaccine is generally administered by providing a single bolus (e.g., intraperitoneal or intramuscular injection, topical administration, or oral administration), followed by one or more booster immunizations. The induction of an immune response can be assessed by examining B and T cell responses that are specific for the antigen according to methods well known in the art. The immunized animal is then challenged with the hepatotrophic pathogen; normally several immunized animals are challenged with increasing titers of the pathogen. The immunized animals and non-immunized control animals are then observed for development of infection, and the severity of infection assessed (e.g., by assessing the titer of the pathogen present, examining human hepatocyte function parameters as described above, etc.). Vaccine candidates that provide for a significant decrease in infection by the pathogen and/or a significant decrease in the severity of disease that results post-challenge are identified as viable vaccines.

Other Uses

Uses of the chimeric animal of the invention that are variations upon or in addition to those described above will be readily apparent to the ordinarily skilled artisan upon reading of the present specification Infectious Disease Diagnosis For example, the chimeric animal can be infected, preferably chronically infected, with a hepatotrophic agent, and used as a source from which the agent can be isolated. This use of the chimeric animal of the invention is particularly useful where, for example, isolation of the pathogen requires biopsy from a human subject or is difficult to obtain in useful amounts; the pathogen cannot be readily cultured in vitro; culturing of the pathogen in vitro (e.g., growth in broth culture or in cultured cells) leads to changes in the pathogen that may affects its pathogenicity and/or clinical relevance; etc. In general, the chimeric animal is inoculated with the isolated pathogen by an appropriate route (e.g., by intravenous, intramuscular, intraperitoneal, or oral administration), preferably by a route of infection that best correlates with the natural route of infection in human disease. After the pathogen establishes infection of the human hepatocytes, and after a sufficient amount of time has passed to allow replication of the pathogen, the pathogen is isolated from the infected chimeric animal by an appropriate method (e.g., isolation from a blood sample, from liver, etc.).

Liver disease diagnosis. The chimeric animal can also be used in the course of diagnosis of liver disease in a human. For example, where the patient suffers from a liver disease of unknown origin or where diagnosis without culturing of the pathogen is not definitive, a sample suspected of containing the causative agent can be isolated from the patient (e.g., from the patient's serum or from a liver biopsy). The sample can be enriched for the suspected agent, fractionated, or otherwise processed to provide it in an administrable form, and administered to the chimeric animal. The chimeric animal can then be evaluated to assess the effect of administration of the sample upon the engrafted human hepatocytes. The effect upon the human hepatocytes can be accomplished by, for example, isolation and examination of serum samples from the chimeric animal, e.g., to assess function of the engrafted human hepatocytes, and/or to detect a pathogen in the animal's serum, e.g., to detect the presence of HCV or other microbial pathogen). The human hepatocytes can also be examined histologically to determine the effect of the patient sample.

Screening using patient samples. The invention can also be adapted to provide for diagnosis and rationale therapy designed on an individualized basis. For example, human hepatocytes obtained by biopsy of a patient (e.g., percutaneous needle biopsy) can be used to produce the chimeric murine host. This chimeric murine host can then be used to evaluate the hepatotrophic pathogen infecting the patient, assess the pathogen's susceptibility to therapeutic agents, and to assess the potential toxicity of the patient's hepatocytes to such therapy. Thus the invention can be designed to facilitate tailoring of therapies most effective against an individual's specific hepatotrophic pathogen complement (e.g., against one or more infecting hepatotrophic pathogens).

Screening for agents that reduce blood lipids. The invention can also be adapted as a system for evaluation of potential therapies of human atherosclerotic vascular (including cardiovascular) disease. Atherosclerosis is the primary cause of heart attack and stroke in the Western world and ultimately is responsible for nearly half the mortality in Canada (Ross (1993) *Nature* 362: 801–809). A positive correlation between high levels of low density lipoprotein (LDL) and atherosclerosis has been realized for several decades (Brown et al. *Ann. Rev. Biochem.* 52: 223–261 (1983)). LDL is derived from very low density lipoprotein (VLDL) in the circulatory system by virtue of a complex series of reactions involving hydrolases, and transfer of lipids and apoproteins among lipoproteins (Fielding et al. (1996) In "Biochemistry of Lipids, Lipoproteins and Membranes", (D. E. Vance and J. E. Vance eds.) pp495–516, Elsevier Science Publishers, Amsterdam). VLDL is secreted into the blood stream via an intricate secretory pathway (Gibbons, *Biochem. J.,* 268: 1–13 (1990); Dixon et al. *J. Lipid Res.* 34: 185–1 (1993); Sniderman et al. *Arterioscler. Thromb.* 13: 629–636 (1993); Yao et al. *Biochim. Biophys. Acta.* 1212:152–166 (1994); Davis et al. (1996) In "Biochemistry of Lipids, Lipoproteins and Membranes" (D. E.

Vance and J. E. Vance eds.) pp. 473–493, Elsevier, Amsterdam; Innerarity et al., *J. Biol. Chem.* 271: 2353–2356 (1996)).

Apolipoprotein (apo) B is a major apoprotein of VLDL and, is the sole apoprotein of LDL. A relationship between high levels of apo B in plasma and the risk of cardiovascular disease has been identified (Sniderman et al., *Proc. Natl. Acad. Sci. USA* 77: 604–608 (1980)). Regression of coronary artery disease has been observed in men aggressively treated with lipid lowering drugs that also cause a decrease in plasma apo B (Brown et al., *N. Engl. J. Med.* 323: 1289–98 (1990)). Thus, there is a positive link among the secretion of apo B from the liver, the ambient concentration of apo B-containing lipoproteins in plasma and the incidence of atherosclerosis. Apo B is a large glycoprotein that is paramount in the assembly and secretion of lipids, including triglyceride and cholesterol of both dietary and endogenous origin. In addition, apo B is important in the intravascular transport and receptor-mediated uptake and delivery of distinct classes of lipoproteins. The importance of apo B thus spans a range of functions, from the absorption and processing of dietary lipids to the regulation of circulating lipoprotien levels. This latter property underlies its relevance in terms of atherosclerosis susceptibility.

Two forms of apo B exist in mammals. Apo B100 represents the full-length protein containing 4536 amino acids and is the exclusive form synthesized in human liver (Young, *Circulation* 82:1574–1594 (1990)). Apo B100 is the major protein constituent of LDL and contains the domain required for interaction of this lipoprotein species with the LDL receptor (Young, 1990, supra). In addition, Apo B100 contains an unpaired cysteine residue, at position 4326, which mediates a covalent interaction with apo(a) and thereby generates another distinct atherogenic lipoprotein, referred to as Lp(a) (Callow et al., *Proc. Natl. Acad. Sci. USA* 91: 2130–2134 (1994); McCormick et al., *J. Biol. Chem.* 271: 28294–28299 (1996)). The small intestine of all mammals, as well as the liver of certain species, synthesize apo B48. In humans, apo B48 circulates in association with chylomicrons and chylomicron remnants, and these particles, by virtue of their content of apo E are cleared by a distinct receptor referred to as the LDL-receptor related protein (Herz et al. *Curr. Opin. Lipidol* 6: 97–103 (1995).

In humans, current evidence indicates that susceptibility to atherosclerosis is most likely due to unfavorable combinations of mutations affecting genes in several pathways, but our knowledge about which genes are involved is limited (Ross, 1993, supra). Due to the ability to introduce or mutate genes, the mouse has become the most common experimental animal model for atherosclerosis research. Wildtype mice on a chow diet do not get atherosclerosis. Three ways to induce atherosclerosis in mice are: diet-induced (Paigen et al., *Proc. Natl. Acad. Sci. USA* 84: 3763–3767 (1987)), apo E deficiency-induced (Piedrahita et al., *Proc. Natl. Acad. Sci. USA*. 89: 4471–4475 (1992); Plump et al., *Cell* 71: 343–353 (1992); Zhang et al., *Science* 258: 468–471 (1992)), and LDL receptor-deficiency induced (Ishibashi et al., *J. Clin. Invest.* 92: 883–893 (1993)). Thus murine transgenic models expressing human genes involved in lipoprotein metabolism have increasingly served as small mammalian models where the spectra of both normal and pathological human serum lipid profiles can be simulated, and in several instances have demonstrated the formation of atherosclerotic lesions. For example, the atherosclerotic lesions in apo E-deficient mice have been well characterized, and they resemble human lesions in their sites of predilection and progression to the fibroproliferative stage. These mouse models of atherosclerosis are being used to identify genes which modify atherosclerosis susceptibility and in the development of antiatherogenic therapies.

The animal model of the present invention can likewise serve as an animal model for hyperlipidemia and artherosclerosis, and can be used to identify candidate agents having activity in reducing the risk of such diseases (e.g., useful in prophylactic treatment) or in treating such diseases (e.g., by lowering blood lipids). Study of serum from the chimeric, transgenic animal model of the invention has demonstrated the presence of the human lipoprotein apoB100. Since this molecule has been established as an important etiologic factor in the development of human atherosclerotic vascular disease, screening for agents that affect apoB100 levels (either quantitatively or qualitatively) can serve to identify agents that can modulate blood lipid levels and thus provide therapy for disease in humans. The positive control for such screening assays can be human serum and, with non-transplanted homozygous Alb/uPA mouse serum serving as the negative control.

Methods for detection of apoB100 are well known in the art. Generally, the assay involves detection of formation of antibody-apoB100 complexes following contacting a biological sample from the animal (e.g., blood, serum, plasma, and the like) with an antibody that specifically binds apoB100. Detection of formation of antibody-apoB100 complexes can be accomplished in a variety of ways (e.g., Western blot, dot blot, RIA, and the like).

Assessing Toxicity of an Agent.

The chimeric animal model of the invention can also be used to screen compounds for toxicity to liver cells, including small molecule therapies for the treatment of liver disorders or for the treatment of any non liver specific human diseases. In general, any compound can be administered to evaluate its toxicity to liver cells. For example, evaluation of an important putative therapy for cancer can be first screened for liver toxicity in the animal model of the invention. Function of the engrafted human liver cells can be assessed as described above (e.g., by assessing levels of human serum albumin, or alpha-1 antitrypsin in the host serum). Injury to liver cells can be assessed by assay of liver specific enzymes in the serum (ALT—alanine aminotransferase), in conjunction with histological assessment for evidence of injury to human cells in the liver. In short, assays to asses liver toxicity can be either functional, histological, or both.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Production of Alb-uPA Transgenic Mice

To generate an Alb-uPA transgenic mouse tolerant to human tissue grafts, mice heterozygous for the transgene (strain TgN(Alb1Plau)144Bri (The Jackson Laboratory)) were crossed with animals from a C.b-17/SCID-beige lineage (strain C.b-17/GbmsTac-scid-bgN7 (Taconic Farms), homozygous). Through a series of backcrosses, the SCID-beige trait was bred to homozygosity as confirmed by quantification of total serum IgG using a sandwich ELISA technique to detect mouse IgG according to methods well known in the art. Quantification of IgG was calculated from a standard curve prepared on each plate using a mouse IgG standard (Cappel). "Leakiness" of the SCID-beige trait was defined as>1% of normal serum IgG (Bosma et al. *Ann. Rev. Immun.* 9:323 (1991)); animals with serum IgG levels above this cutoff were euthanised. At each step, animals carrying the Alb-uPA transgene were identified by PCR analysis of genomic DNA extracted from tail biopsies, using two 18-mer primers that amplify a 151 bp product from the 3' UTR of the transgene construct (Jackson Laboratories technical support). Although the homozygous Alb/uPA trait has been previously associated with a high perinatal mortality rate secondary to bleeding complications and liver failure (Heckel et al. *Cell* 62:447 (1990)), we found that in our scid/bg/Alb-uPA animal colony neonatal mortality was approximately 30%. The colony providing animals was developed initially with heterozygous breeders, but with moderate neonatal mortality in homozygous mice, the colony was evolved to completely homozygous. Animals were housed in virus/antigen-free conditions, and were cared for in accordance with the guidelines established by the Canadian Council on Animal Care (1993). All animal experiments describe Herein were performed with approval from the University of Alberta Animal Welfare Committee.

Human hepatocytes for transplantation were obtained with approval from the University of Alberta Faculty of Medicine Research Ethics Board. Segments of human liver tissue (15–20 cm$^3$) obtained at laparotomy were perfused with ice-cold Ca/Mg-free PBS containing 0.5 mM Na$_2$EDTA. Prominent perfusing vessels were cannulated and the tissue was perfused for 30 minutes with recirculating carrier solution (35 mM NaCl, 3.5 mM KCl, 2.5 mM CaCl$_2$, 50 mM HEPES, pH 7.6) containing 0.38 mg/mL Liberase CI collagenase (Boeringer-Mannheim) (Ryan et al. *Surgery* 113:48 (1993); Seglen et al. *Meth. Cell Biol.* 13:29 (1976)). Hepatocytes were filtered through 100 µm stainless steel mesh, purified by density-gradient centrifugation (Percoll, density 1.04 g/mL; Sigma) at 400 g for 5 minutes, and washed twice in ice-cold HBSS prior to suspension in Belzer-University of Wisconsin solution (DuPont) at 0° C. for short-term storage prior to transplantation. Cell counts and viability were confirmed by trypan blue exclusion prior to transplantation; final viability was routinely >80%.

In initial experiments, animals homozygous for the SCID trait and heterozygous for the Alb-uPA transgene were crossed, and 7 day-old progeny were transplanted with 1×10$^6$ freshly isolated viable human hepatocytes. Transplantation was accomplished by intrasplenic injection. Intrasplenically injected hepatocytes rapidly translocate to the liver via the portal venous system and engraft into the parenchyma surrounding terminal portal venules (Ponder et al. *Proc. Natl. Acad. Sci. USA* 88:1217 (1991); Gupta et al. *Transplantation* 50:472 (1990)). Since the mortality associated with intrasplenic injection is minimal, the spleen was selected as the optimal site for implantation. Accordingly, offspring (5–17 days old) were anesthetized with Halothane/O$_2$, and a small left flank incision was made. Under operating magnification, 1×10$^6$ viable hepatocytes were injected into the inferior splenic pole with a 27 g butterfly injection set (Becton-Dickinson), and a single sterile titanium clip was placed across the injection site for hemostasis. The spleen was returned to the abdomen, and the flank incision was closed in two layers.

Since the production of albumin is an exclusive property of hepatocytes (Clement et al, *Hepatology* 4:373 (1984); Gunsalas et al. *Nature Medicine* 3:48 (1997)), detection of human albumin (HA) in serum samples by selective immunoprecipitation and Western blotting was employed as an indicator of graft cell function. Recipient mice were initially sampled by jugular venous puncture at four weeks post-transplant, and at weekly intervals thereafter. Aliquots of mouse serum (20µl) were incubated with an anti-human albumin monoclonal antibody (Clone HSA-9; Sigma), and antigen-antibody complexes were precipitated with protein G-agarose (Boehringer-Mannheim). Immunoprecipitates were heated for 5 minutes at 98° C. in SDS buffer containing 0.2 M dithiothreitol, separated by SDS-polyacrylamide gel electrophoresis and transferred to nitrocellulose. Western blots were prepared in standard fashion (Coligan et al. *Current Protocols in Immunology* (Wiley, New York, 1997), vol. 2, chap. 8.10.7) using a second anti-human albumin monoclonal antibody (Clone HSA-11; Sigma) conjugated to biotin as the primary. A streptavidin-HRP conjugate (Pierce) was employed as the secondary, and chemiluminescent reagents (Pierce) were used for signal detection.

A strong HA signal was demonstrated in the serum of 4/7 transplanted littermates, indicating the presence of significant numbers of functional human hepatocytes; subsequent genotype analysis revealed that all HA-positive animals carried the Alb-uPA transgene, whereas all the animals negative for HA were also negative for the transgene. Clear HA bands were detected as early as two weeks post-transplant, with an increase in intensity over the 4–6 week timepoints, suggesting vigorous expansion of the primary cell grafts (FIG. 1). These findings indicated that the microenvironment within the Alb-uPA liver was sufficient to stimulate human hepatocytes to begin rapid proliferation, and that there was the potential to support the establishment of long-term human grafts.

To confirm proliferation and estimate the extent of replacement of murine parenchyma with human-derived cells, formalin fixed, paraffin embedded sections of recipient livers were obtained at various times after transplantation and immunostained with a monoclonal antibody specific for human hepatocytes. Segments of mouse liver were fixed in 10% formalin and embedded in paraffin. Sections 5u thick were stained with hematoxylin and eosin (H&E) in standard fashion. Selected sections were treated with an endogenous avidin/biotin blocking kit (Zymed Laboratories, Inc.) and immunostained with a monoclonal anti-human hepatocyte antibody (DAKO, 1:20 dilution); bound antibody was detected using the Super Sensitive Immunodetection System (BioGenex)

The results are shown in FIGS. 2A–2F. In animals carrying the transgene, clusters of cells staining positive with the anti human hepatocyte antibody (darkly stained cells) were scattered uniformly throughout the host liver at two weeks post-transplant, comprising an estimated 2–3% of all hepatocytes. At four weeks the percentage of positive-staining cells had increased, covering from 20 to 60% of the total surface area of individual sections. The interface between human and mouse cells was distinct, with cords of human cells extending into the surrounding murine parenchyma. Individual human cells maintained a normal appearance and developed sinusoidal architecture, although portal triad structures were notably absent from the regenerating nodules. This latter observation was not unexpected, since human-derived nodules are the result of clonal expansion of individual hepatocytes (Sandgren et al. Cell 68:245 (1991)). These nodules would contain no bile duct or endothelial precursor cells; such structures would be host-derived and therefore marginalized around proliferating human tissue.

Analysis of human hepatocyte graft function. Two different serum-based assays were used to evaluate the human hepatocyte graft in our chimeric mice. The first assay is a dot blot assay measuring human serum albumin; the second assay is an ELISA assay measuring human alpha-1 antitrypsin (hAAT). The same mice were assayed at 6 and 12 weeks post transplant.

The dot blot assay was performed by diluting 2 μl of sample or standard into 40 μl of reducing buffer and heat for 5 min at 100 degrees (standards=known amounts of human albumin in blank mouse serum). A 2 μl volume of solution was blotted onto Nitrocellulose membrane and allowed to dry for 15 min. The membrane was soaked in Western Transfer Solution for 10 min, and then blocked with 3% TBST for 1 hour. The membrane was washed, and monoclonal antibody applied to reduced human albumin at 1:5000 for 2 hours. After washing, horseradish-peroxidase-streptavidin at 1:10000 was applied for 1 hour, followed by washing and developing with ECL-PLUS chemiluminescent solution. The membrane is then read using a phosphoimager. The standard curve was plotted using standards and use this curve to calculate sample values.

The ELISA was performed by coating plates with polyclonal goat—anti-hAAT antibody at 1:1000 overnight, washing, and then blocking with TBST/milk buffer overnight. After washing, the standards and samples, diluted appropriately in milk buffer, were applied and incubate for 2 hours at RT. After washing, secondary antibody linked to HRP at 1:300 (diluted in milk buffer) was applied and incubated for 2 hours at RT. After washing, TBMD substrate was added, and the reaction stopped at 5 minutes by addition of 1 M $H_2SO_4$ The plate was read at 450 nm. A standard curve was plotted using standards and this curve used to calculate sample values.

The table below shows the results obtained with each assay.

| Mouse | Age post-transplant | DOT BLOT (μg/ml human albumin) | ELISA (μg/ml AAT) |
| --- | --- | --- | --- |
| DfRP (HOMO) | 6 weeks | 2283 | 244 |
|  | 12 weeks | 1717 | 173 |
| CfRP (HOMO) | 6 weeks | 385 | 86 |
|  | 12 weeks | 594 | 74 |
| CfRM (HOMO) | 6 weeks | undetectable | 0.7 |
|  | 12 weeks | dead | dead |
| BfLM (HOMO) | 6 weeks | 154 | 17 |
|  | 12 weeks | 382 | 40 |
| BmLP (HOMO) | 6 weeks | 608 | 45 |
|  | 12 weeks | 767 | 96 |
| AfRP (HETERO) | 6 weeks | 99 | 7 |
|  | 12 weeks | undetectable | 1 |
| AmLM (Hetero) | 6 weeks | 200 | 14 |
|  | 12 weeks | undetectable | 2 |

HOMO indicates animal is homozygous for the transgene; HETERO indicates the animal is heterozygous for the transgene. Both assays show in general the trends are the same, showing a much higher production of human-derived proteins in the homozygote for the uPA transgene compared with the heterozygotes.

Conclusion. This example demonstrates successful transplantation of the immunocompromised, scid/bg/Alb-uPA mice with human hepatocytes.

Example 2

Persistence and Proliferation of Engrafted Human Hepatocytes

To determine the long-term outcome of initial successful engraftment and proliferation, a second litter of 8 animals was transplanted in similar fashion. The hepatocytes available for use at the time of this experiment were obtained from a patient who was a chronic carrier of hepatitis B virus. The patient exhibited both a positive serum HBsAg levels and negative serum HBV DNA, indicating a chronic carrier state without active viral replication (Davis, South. Med. J. 90:866 (1997)).

Two randomly selected animals were sacrificed at 4 weeks for histologic analysis, and the remaining 6 animals were followed at weekly intervals. Serum samples were subjected to Western blot as described above, and the HA bands from Western blots quantified using image analysis software and band densitometry (Umax Astra 1200S scanner and VistaScan DA v.1.2.2 imaging software (UMAX Copr, Fremont, Calif.). Quantification of HA peaks was performed using NWR Image 1.60/fat software (National Institute of Health), and normalized to a 50 ng HA standard present on each blot.

Figure 3:
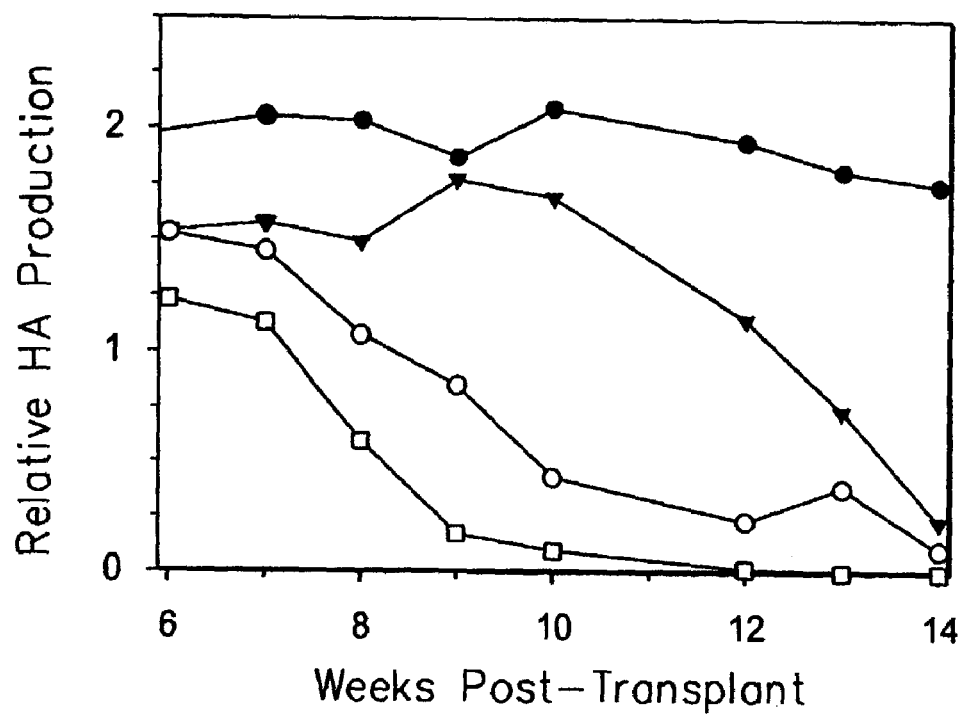
FIG. 3 is a graph illustrating production of albumin from human hepatocyte grafts (1×10⁶ cells) in four recipients carrying the Alb-uPA transgene.

Again, initial graft proliferation was seen only in the 4 animals which carried the transgene. In these animals, HA signals remained near maximal to 8 weeks at which point two distinct patterns of graft function emerged (FIG. 3; Mouse 3, open square; Mouse 4, closed triangle; Mouse 5, open circle; Mouse 6, closed circle).

Figure 4:
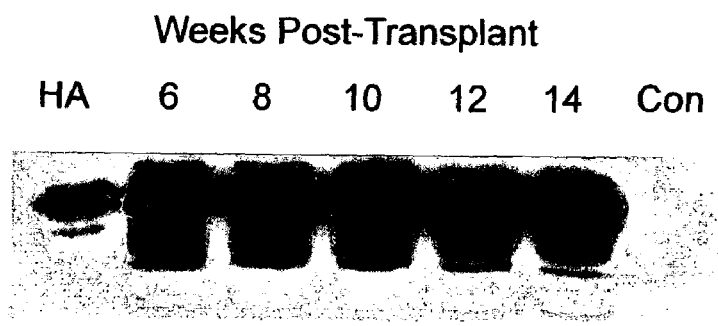
FIG. 4 is a Western blot of HA production in an Alb-uPA-positive recipient post-transplant showing sustained signal intensity. HA—human albumin standard (50 ng); Con—nontransplanted mouse serum control.

In three animals graft function began to slowly decline, with extinction of the HA signal at 10, 15 or 16 weeks. In contrast, the fourth transgenic animal (mouse no. 6) showed maximal HA production at all measured timepoints (FIGS. 3 and 4), indicating stable engraftment of human hepatocytes. Sustained graft function repeatedly occurred in approximately 25% of animals carrying the transgene. The proliferative signal for the transplanted hepatocytes is likely dependent on overall expression of the transgene, and is reduced as host-derived hepatocytes spontaneously delete the transgene.

In order to assess whether the transplanted mice supported the HBV infection of the HBV-infected, transplanted cells, serum samples from all transplanted mice were screened for hepatitis B surface antigen (HBsAg) production by sandwich ELISA. Aliquots of serum (20 μl) were tested for presence of HBsAg using a sandwich ELISA kit (Heprofile HbsAg; ADI Diagnostics) with plate analysis performed using a Dynatech MRX microplate spectrophotometer (Dynex). Both positive and negative human serum controls, as well as negative murine serum controls were included in assays.

The results are summarized in Table 1. Negative human and mouse serum controls range from 0.04–0.05 absorbance units; positive human controls range from 0.30–0.40 absorbance units.

TABLE 1

Analysis of serum markers of hepatitis B infection following transplantation of mice with HBV-infected human hepatocytes.

| Mouse | Alb-uPA Genotype | HA Expression Pattern | HBsAg Level Post-Transplant* | | | | |
|---|---|---|---|---|---|---|---|
| | | | 6 wk | 8 wk | 10 wk | 12 wk | 16 wk |
| 1 | − | Absent | ND | 0.04 | 0.04 | 0.04 | ND |
| 2 | − | Absent | 0.04 | 0.03 | ND | 0.02 | ND |
| 3 | + | Transient | 0.04 | 0.03 | 0.08 | 0.05 | ND |
| 4 | + | Transient | 0.12 | 0.04 | 0.07 | 0.04 | ND |
| 5 | + | Transient | 0.04 | 0.03 | ND | 0.04 | ND |
| 6 | + | Persistent | 0.13 | 0.13† | 3.18† | 3.78† | 3.44† |

Key: HA—human albumin; ND—not done; *HBsAg levels expressed as absorbance units.
†Samples positive for HBV DNA by PCR analysis.

As expected, control (Alb-uPA negative, nos. 1–2) mice had undetectable HBsAg levels and the three transgenic animals with transient graft function showed only sporadic minimal increases during weeks 6–12. However, the transgenic mouse with the pattern of sustained graft function (mouse no. 6) demonstrated clearly elevated levels at all time points measured, with an abrupt increase after 8 weeks to persist well within the range of HBsAg levels in actively infected human controls. The abrupt increase was suggestive of restoration of active viral replication.

To confirm active replication samples of serum taken from this animal at 8, 10, 12 and 16 weeks were analyzed by PCR for the presence of HBV DNA. DNA isolated from 12.5 μl of mouse serum were subjected to PCR using HBV-specific primers and amplification conditions previously described (Tipples et al. Hepatology 24:714 (1996)). All analyses were performed in blinded fashion. All four serum samples were strongly positive for the presence of viral DNA (data not shown). This result was of special interest in that despite not actively replicating within its human donor, the virus was reactivated within the immunodeficient murine host. This reactivation may have been the result of inadequate antiviral immunity, similar to what is observed in chronic HBV carriers given pharmacologic immunosuppression after organ transplantation (Terrault et al. *Gut* 40:568 (1997)).

This example thus demonstrates that human hepatocytes transplanted into chimeric, transgenic mice can support HBV viral replication.

Example 3

Establishing Primary HCV Infection

The success above in production of a chimeric animal that supports HBV replication in the chimeric mouse supports the use of the animal as a model of HBV. However, the vast differences between HBV and HCV discussed above (Background) meant that there could be no reasonable expectation that the animal model would be susceptible to HCV infection through a normal route of infection (e.g., intravenous transmission) or that the chimeric liver could support an active HCV infection, particularly in view of the failure of others to develop HCV animal models and the rarity of cell systems for HCV. The comparative success with HBV animals models and the repeated failures of others with HCV animal models indicate that one can not simply extrapolate from HBV to HCV. Thus, an attempt was made to establish a primary HCV infection in mice with chimeric livers using virally-infected human serum.

Seven littermates were transplanted at 7 days of age with human hepatocytes isolated from a patient serologically-negative for both HCV and HBV infection. After confirming initial graft function in 5/7 animals at 6 weeks post-transplant, all mice were inoculated intravenously with 0.25 mL of human serum obtained from an unrelated HCV-positive donor. The HCV-positive status of the human serum donor was confirmed positive for HCV RNA by PCR, with viral titers of $1 \times 10^7$ copies per ml serum. Thus, each mouse was inoculated with approximately $2.5 \times 10^6$ viral particles. Serum samples taken from all seven mice at 11, 12 and 13 weeks post-transplant (5, 6 and 7 weeks post-infection) were analyzed for the presence of HCV RNA by RT-PCR analysis using the Cobas Amplicor system (Roche Diagnostics), according to the manufacturer's instructions. Two nontransplanted mice served as mock-infected controls.

Of the five animals with good initial engraftment, four showed the pattern of transient graft function and again one animal demonstrated HA levels at maximal intensity over all measured timepoints. All three samples taken from the animal with sustained human chimerism as reflected by persistent human albumin levels in serum were strongly positive for HCV RNA, and persistently positive at weekly intervals to 36 weeks. RT-PCR analysis was uniformly negative for animals negative for the Alb-uPA transgene or that only transiently expressed the HA marker for the transgene. As 6 animals were negative for HCV RNA, the possibility of the positive RT-PCR signals in the seventh animal originating from residual virus from the inoculum is remote. This example supports the conclusion that this animal had developed and at 23 weeks post-transplantation and 20-weeks post-infection, is propagating an active HCV infection at $1.2 \times 10^5$–$1.8 \times 10^5$ virion/ml serum.

This series of experiments establishes the capacity of the SCID-beige/Alb-uPA transgenic mouse to generate and sustain a chimeric human liver for prolonged and perhaps indefinite periods of time after transplantation of human hepatocytes. These chimeric organs can be infected de novo with HCV-positive human serum, and can support long-term replication (e.g., for a period of weeks or months as opposed to a few days) of human-specific hepatotrophic viruses at levels that can be equated to clinical levels in humans. HCV viral particles can be detected in serum, blood, or other blood-derived fraction by standard techniques, which techniques can be automated to facilitate more rapid screening. For example, the samples from the HCV-infection host can be diluted with known noninfected serum (e.g., about two to four fold dilution), to provide a sample volume adequate for use in an automated machine, and provide signal strengths in the assays indistinguishable from random human samples.

Long-term replication of HCV in the model of the invention (e.g., for a period longer than about 4 weeks, generally longer than about 12 weeks, e.g., about 3 months to 6 months or more) allows for the use of the model in the testing of drugs over extended periods of time, which period may be necessary for adequate drug development. For example, the effect of administration of interferon-α (particularly interferon-α2b), an anti-HCV therapy, is generally only detectable in humans after about 12 weeks of therapy. In an animal model that sustained viral replication for only a few days or weeks and/or exhibited inconsistent viral production, it would be difficult or impossible to determine if changes in viral titers were due to a candidate therapeutic or to normal fluctuations in titer inherent in the animal model. The present invention provides a model that avoids this problem.

In summary; to the best of the inventors' knowledge, this is the first report of a non-primate animal model that is susceptible to HCV infection by a normal route of infection. The model is clinically relevant (e.g., can be infected by a normal route of infection, and supports persistent HCV infection similar to that observed in humans), can be produced regularly and reliably in substantial numbers, and will allow investigators to directly explore strategies for inhibiting viral replication in vivo.

Example 4

HCV Infection of Alb-uPA Mice

In this Example, the work above was expanded further to demonstrate that the animal model of the invention can support replication of HCV.

Methods and Materials

The following Methods and Materials were used in this example.

Development of scid/Alb-uPA strain. Animals were housed in virus/antigen-free conditions, and cared for in accordance with the guidelines established by the Canadian Council on Animal Care (1993). Approval for animal experimentation was obtained from the University of Alberta Animal Welfare Committee.

Hemizygous Alb-uPA mice (strain TgN(Alb1Plau) 144Bri, The Jackson Laboratory) were crossed with homozygous scid-bg mice (strain C.b-17/GbmsTac-scid-bgN7, Taconic Farms), and progeny carrying the Alb-uPA transgene were identified by PCR analysis of genomic DNA extracted from tail biopsies (Jackson Laboratories technical support). Through backcrossing, the scid trait was bred to homozygosity as confirmed by quantification of total serum IgG using a sandwich ELISA. Animals with >1% of normal serum IgG were euthanized.

Isolation and purification of human hepatocytes. Ethical approval for use of human tissue was obtained from the University of Alberta Faculty of Medicine Research Ethics Board; informed consent was obtained from all hepatocyte donors. Segments of human liver tissue (15–20 cm$^3$) were obtained from regions of hepatic resection specimens which would normally be discarded after pathologic examination; the majority of operations were performed for intrahepatic malignancies.

After rapid cooling of resected specimens, hepatocytes were isolated and purified by standard two-step collagenase-based perfusion (Seglen *Methods Cell Biol.* 13:29–83 (1976); Ryan et al Surgery 113:48–54 (1993)) using 0.38 mg/mL Liberase CI (Boehringer-Mannheim) in the collagenase perfusate. After purification, cells were washed and suspended in Belzer-UW solution (DuPont) at 0° C. for short-term storage prior to transplantation. Cell counts and viability were confirmed by hemocytometer and trypan blue exclusion; final viability was routinely >80%.

Transplantation of human hepatocytes. Recipients (5–14 days old) were anesthetized with halothane/O$_2$, and a small left flank incision was made. Under operating magnification, 1×10$^6$ viable hepatocytes were injected into the inferior splenic pole with a 27 g butterfly injection set (Abbott), with a single sterile titanium clip placed across the injection site for hemostasis. The spleen was replaced and the flank incision closed in two layers.

Detection of HA in mouse serum by immunoprecipitation and Western blot. Mouse serum (20 µl) was incubated with monoclonal anti-HA antibody (Clone HSA-9, Sigma) and antigen-antibody complexes collected with protein G-agarose beads (Boehringer-Mannheim). Under reducing conditions, immunoprecipitates were separated by SDS-PAGE and transferred to nitrocellulose. Western blots were prepared using a biotinylated monoclonal anti-HA antibody (Clone HSA-11, Sigma), with a streptavidin-HRP conjugate and chemiluminescent substrate (Pierce) for signal detection.

Determination of zygosity of the Alb-uPA transgene. Mouse DNA (3 ug) was digested with PvuII, size fractionated on 0.7% agarose gel, transferred to Hybond-N+ membrane (Amersham Life Science), and hybridized to a [$^{32}$P]—labeled probe from the final intron of the uPA gene (positions 7312–7920, GenBank accession M17922). A band of 2.88 kb was derived from uPA transgenes (T) and a 2.53 kb band from endogenous uPA genes (E); hybridization was quantified with a Fuji phosphoimager and Image Gauge Software.

Immunohistochemistry. Mouse liver biopsies were fixed in 10% formalin and embedded in paraffin. Sections 5µ thick were stained with hematoxylin and eosin (H&E) in standard fashion. Selected sections were treated with an endogenous avidin/biotin blocking kit (Zymed Laboratories, INC.) and immunostained with a monoclonal anti-human hepatocyte antibody (DAKO, 1:20 dilution); bound antibody was detected using the Super Sensitive Immunodetection System (BioGenex).

Protein dot-blot assay for quantitation of HA production. Samples of mouse serum (2 µl) were incubated for 5 min at 100° C. in 40 µl reducing buffer, and 2 µl aliquots were blotted in triplicate onto nitrocellulose. Dried membranes were soaked in transfer buffer, blocked with 3% PBS-Tween, and prepared as Western blots. Chemiluminescence was quantified using a STORM phosphoimager, from a standard curve prepared on each blot.

Quantitative analysis of positive strand HCV RNA in mouse serum. Quantitative HCV analysis was performed in blinded fashion by the Alberta Provincial Laboratory of Public Health (Edmonton, Alberta, Canada), or the Canadian Center for Disease Control (Winnipeg, Manitoba, Canada). Analysis was performed on serum samples using the Cobas Amplicor HCV Monitor system (Roche Diagnostics) according to manufacturers instructions.

Detection of negative-stranded HCV RNA by thermostable rTth reverse transcriptase RNA PCR. Total RNA was isolated from mouse liver biopsies or infected human serum using TRIZOL (Gibco BRL). RT-PCR was performed using a thermostable rTth reverse transcriptase RNA PCR kit (Perkin Elmer) according to manufacturer's instructions. Positive-strand RNA was detected with an antisense (5'-CTCGCAAGCCCCTATCAGG-3' (SEQ ID NO:1)) primer and negative-strand with a sense (5'-GAAAGCGTCTAGC-CATGGCGT-3' (SEQ ID NO:2)) primer for reverse transcription 14. Strand-specific cDNA was amplified by adding the other primer to target a 240-base pair (bp) region of the 5' non-coding region (NCR) and subjected to 35 cycles at 95° C. for 30s, 66° C. for 45s and 70° C. for 90s, followed by 70° C. for 5 minutes. Reaction products were loaded onto a 2% agarose gel, transferred to Hybond-N+ nylon membrane (Amersham Pharmacia Biotech) and hybridized with an α-$^{32}$P-labelled DNA probe for HCV 5' NCR at 42° C. overnight.

Detection of negative-stranded HCV RNA by RNase protection assay. Total RNA was isolated from mouse liver using Trizol Reagent (GIBCO/BRL) and from HCV-infected human serum using QIAamp Viral RNA Mini Kit (Qiagen), each according to manufacturer's protocol. Extracted RNA was probed with 32P-labeled, gel-purified antisense riboprobe (detection of (+) strand), sense riboprobe (detection of (−) strand), and/or β-actin antisense riboprobe.

Plasmid Constructs. Three plasmid constructs were prepared for in vitro transcription of truncated HCV RNA. HCVPfix/KS+ is a construct originally developed in our lab for expression studies of HCV serine proteinase. Total RNA prepared from fresh serum obtained from HCV-infected patients (Chomczynski et al. *Anal Biochem* 162, 156–159 (1987)) was denatured at 95° C. for 5 min. cDNA synthesis was performed in a 20 µl reaction volume with AMV super reverse transcriptase (Molecular Genetic Resources) at 42° C. for 90 min. The antisense oligonucleotide primer used was 5'-TCTCTGTCGACTCACTGGGGCACTGCTG-GTGG-3' (SEQ ID NO:3) (3'primer). PCR was performed in a total volume of 100 µl and contained 2 µl of the final cDNA reaction mixture, 20 mM Tris-HCl (pH 8.4), 50 mM KCl, 1.5 mM MgCl2, 200 µM of each deoxyribonucleoside triphosphate, 0.5 µM of 3'primer and 5'primer (5'-GGAAT-TCGCGACGACGATGACAAGGCACCCAT-TACGGCGTATGCCCAGCA GACAAGGGGCCTCTT-3' (SEQ ID NO:4)), and 2.5 U Taq DNA polymerase (GIBCO/BRL). The 5' primer added an enterokinase cleavage site, and the entire 623 bp fragment was cloned into the Eco R1 and Sal 1 sites of pBluescript KS+ (Stratagene, PDI).

The remaining two plasmids were constructed using a PCR strategy to obtain a region of the highly conserved 5' noncoding region (NCR) of HCV RNA from pCV-H77C (Masayuki et al. *J. Proc Nat Acad Sci USA* 94, 8738–8743 (1994)). PCR components were as above except the template used was 100 ng pCV-$H_{77}$C and primers were 5'-GAAAGCGTCTAGCCATGGCGTTAG-3' (SEQ ID NO:5) (5' primer) and 5'-GGCACTCGCAAGCACCCTAT-CAGGC-3' (SEQ ID NO:6)(3' primer). Both orientations of the 245 bp product were TA-cloned into pCR2.1 TOPO using a commercially available TOPO TA Cloning kit (Invitrogen) to generate pCR 2.1/NCRsense and pCR 2.1/NCRantisense plasmids. All clones were confirmed by DNA sequencing (University of Alberta DNA Core Facility).

Preparation of Riboprobes and Truncated HCV RNA Transcripts. Riboprobes were prepared by in vitro transcription using T7 RNA polymerase (Promega) according to the manufacturer's instructions, in the presence of [32P]UTP. For detection of (+) strand HCV RNA, a 383-nt antisense riboprobe was transcribed from Kpn I digested pCR 2.1/NCRantisense and for (−) strand, a 636-nt sense riboprobe was transcribed from Sal1 digested HCVPfix/KS+. For detection of β-actin, linearized pTRI-Actin-Mouse (AMBION) was used to generate a 304 nt riboprobe. To demonstrate specificity of strand-specific detection of HCV RNA, radioinert sense and antisense riboprobes were also prepared. Briefly, pCR2.1/NCR sense/antisense were digested with Kpn I and HCVPfix/KS+ was digested with Sal I prior to in vitro transcription using T7 RNA polymerase. Additionally, HCVPfix/KS+ was linearized with Eco R1 and in vitro transcribed using T3 RNA polymerase (Promega). All in vitro transcription reactions were 1 hour at 37° C. followed by treatment with RNase-free DNaseI (RQ1 DNase, Promega) for 30 min at 37° C. Labeled riboprobes were gel purified and radioinert HCV RNA riboprobes were precipitated with 2.5 volumes of absolute ethanol after adding 0.5 volumes of 7.5 M ammonium acetate. Integrity of radioinert in vitro transcribed RNAs was evaluated by electrophoresis through a 1% agarose gel. RNA samples were denatured and hybridized overnight at 42° C., and RNase digestion was performed using an RNase protection assay kit (AMBION RPA III Kit). Products were resolved on a 5% polyacrylamide gel containing 8 M urea and exposed to Kodak X-Omat AR film.

Production of Transgenic Mice and Transplantation of Human Hepatocytes

Mice carrying Alb-uPA were crossed with animals from a C.b-17/scid-bg lineage, and through selective backcrosses bred the scid trait to homozygosity. In initial experiments, homozygous scid animals carrying the Alb-uPA transgene in hemizygous fashion were crossed, and litters of 4–12 day-old progeny were transplanted intrasplenically with 0.5–1× $10^6$ freshly isolated viable human hepatocytes. Human albumin, produced exclusively by human hepatocytes, was employed as an indicator of graft function.

In a pilot study of 36 transplants, a strong HA signal at 4–5 weeks post-transplant was demonstrated in the serum of 19 recipients. HA bands were detected as early as two weeks post-transplant and increased in intensity over the 4–6 week timepoints suggesting graft expansion (FIG. 5). Blinded genotype analysis revealed that all strongly HA-positive animals carried Alb-uPA whereas the remainder did not.

Despite initially strong HA signals, some graft recipients had extinction of signal at around 14 weeks, while a second subset maintained strong signals beyond 30 weeks; representative results are shown in FIG. 7. As these graft recipients were progeny of heterozygous crosses, the divergence in graft survival as the result of zygosity of the Alb-uPA transgene was tested. Using a [$^{32}$P]—labeled probe derived from the final intron of the uPA gene, transgenic and endogenous uPA were distinguishable by Southern blot analysis, and the signal ratio could be used to determine the zygosity of the transgene array (FIG. 6). Genomic DNA analysis confirmed that animals demonstrating sustained human engraftment were homozygous for Alb-uPA, whereas the subset with failing graft function were hemizygous.

Examination of sections from transplanted homozygote livers revealed large nodules of hepatocytes arranged in typical cord-like structures. Within nodules, hepatocyte cytoplasm and nuclei appeared histologically normal in contrast to surrounding tissues, where cells were obviously smaller, with vacuolated cytoplasm and pyknotic nuclei. To delineate human cells, we immunostained sections with a monoclonal anti-human hepatocyte antibody which intensely stained control human liver but had no substantial cross-reaction with non-transplanted homozygous mouse liver. This demonstrated that the nodules were clearly of human origin, expanding outward into and compressing surrounding murine-derived tissues. While the large human nodules contained healthy hepatocytes, all biliary tract and portal structures appeared to be host-derived.

HCV Infection

With evidence of prolonged human engraftment, mice were infected with serum from HCV-infected human donors. Non-infected human hepatocytes were transplanted into 27 offspring from heterozygous crosses, and at 6 weeks after transplantation all mice were inoculated intravenously±intraperitoneally with 0.25 ml of human serum obtained from one of two unrelated HCV-positive donors (viral genotypes 1a and 6a). Selected serum samples between 3 and 40 weeks after inoculation were analyzed for the presence of positive-stranded HCV RNA by RT-PCR; results of the experiment are summarized in Table 2. Graft duration was defined as the period of HA detectability by immunoprecipitation/Western blot procedure.

TABLE 2

Infection of homozygous mice with human HCV

| Alb-uPA Genotype | n | Initial HA Signal | Median Graft Duration (weeks) | HCV RNA (RT-PCR) |
|---|---|---|---|---|
| −/− | 8 | None* | 0 | 0/8 |
| +/− | 15 | Strong | 15.5 | 0/15 |
| +/+ | 4 | Strong | 30.5† | 4/4‡ |

*3/8 animals had a single weak HA signal at 5 week timepoint only
†p < 0.001 vs. hemizygotes and wild-type by Kruskal-Wallis test
‡p < 0.001 vs hemizygotes and wild-type by Pearson Chi-square test All 8 wild-type controls had no evidence of initial graft function and were persistently negative for HCV RNA. Hemizygous animals had initially strong HA signals, but progressively lost signal intensity over time to a median graft duration of 15.5 weeks; (+) stranded HCV RNA was not detected in any of these animals over multiple timepoints. In sharp contrast, all four animals homozygous for the Alb-uPA transgene demonstrated sustained human chimerism (median 30.5 weeks) and were positive for HCV RNA by serum RT-PCR analysis. Quantitative HCV RNA analysis revealed viral levels ranging from $1.4 \times 10^3$ to $1.4 \times 10^6$ RNA copies/ml, well within the range of infected humans. Successful infections were established with both genotypes of viral inoculum and duration of infection ranged from 10–21 weeks in this initial cohort of four animals.

HCV Infection of Animals Homozygous or Hemizygous for the Alb-uPA Transgene

While positive-stranded HCV RNA was persistently demonstrable in homozygous animals, HCV RNA was undetectable in hemizygotes. We hypothesized that hemizygotes fail to support HCV replication at detectable levels as a result of diminished initial engraftment and earlier graft loss. To test this hypothesis, a protein dot-blot assay was developed using chemiluminescence and phosphorimaging to more accurately quantify HA production. After transplanting $1 \times 10^6$ cryopreserved human hepatocytes from a single human donor into 21 recipients (15 homozygotes and 6 hemizygotes), randomly selected animals were sampled for quantitative HA analysis and/or sacrificed for immunohistochemical analysis. Results of this experiment are shown in FIG. 8.

Figure 8:
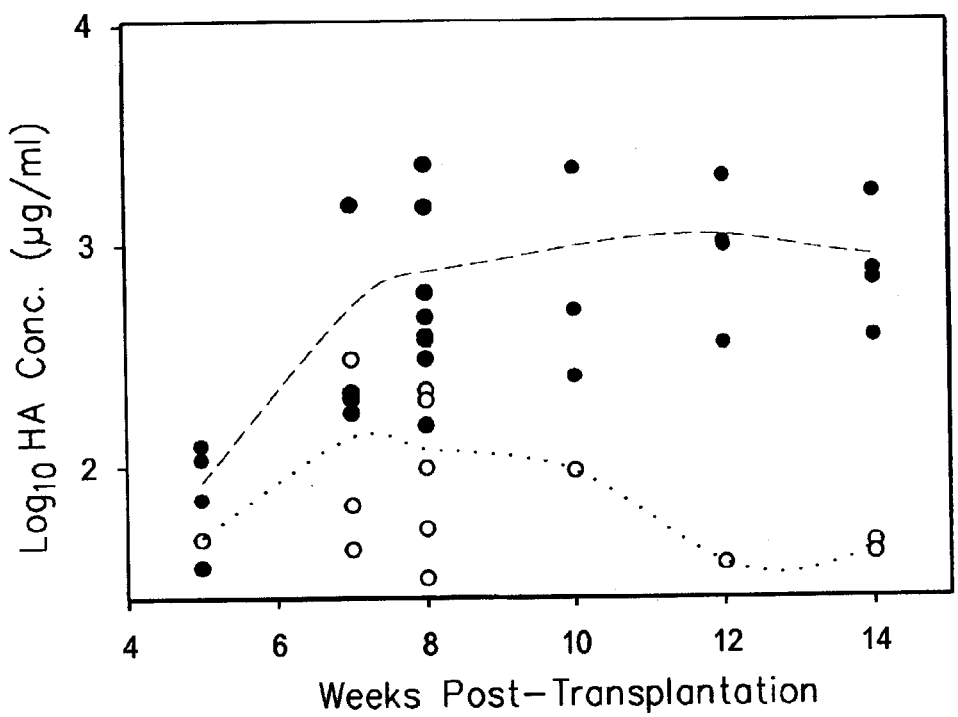
FIG. 8 is a graph showing a vertical scatterplot of quantified HA production from individual homozygous (closed circles) or hemizygous (open circles) recipient mouse serum samples. Median trend lines are shown for both groups.

While hemizygous and homozygous animals initially had similar HA signal intensities, by 5–6 weeks a clear dichotomy became apparent and by 10–12 weeks HA signals in homozygous mice were more than an order of magnitude higher than hemizygotes (FIG. 8). Random liver sections from homozygous and hemizygous recipients sacrificed at selected points after transplantation were immunostained with a monoclonal anti-human hepatocyte antibody to estimate the percent replacement of murine liver with human tissue. These immunohistochemical data confirmed the protein dot-blot findings, with human cells occupying substantial portions (>50%) of cross-sectional liver area in homozygous animals. In distinct contrast, examination of multiple sections of tissue from heterozygous recipients revealed only minimal evidence of human engraftment. Together, these studies suggest a substantial advantage in both the magnitude and duration of human hepatocyte engraftment for homozygous Alb-uPA recipients compared to their heterozygous counterparts.

By transplanting into the progeny of heterozygous crosses, successful infections were established in 4/27 mice, all homozygotes. This success rate would make the model too cumbersome for routine use. As a result of the quantitative advantage in graft size ascribed to homozygous mice, the breeding colony was shifted towards exclusive production of homozygous Alb-uPA mice. Using the dot-blot assay described above to screen early for high-level hepatocyte engraftment (HA levels >250 μg/ml), ~75% of HCV-inoculated animals developed persistent viral titers $>3 \times 10^4$ copies/ml, with many $>10^6$ copies/ml. The remainder of the viral studies were performed in homozygous recipients.

Confirmation of Long-Term Persistence of HCV

Figure 9:
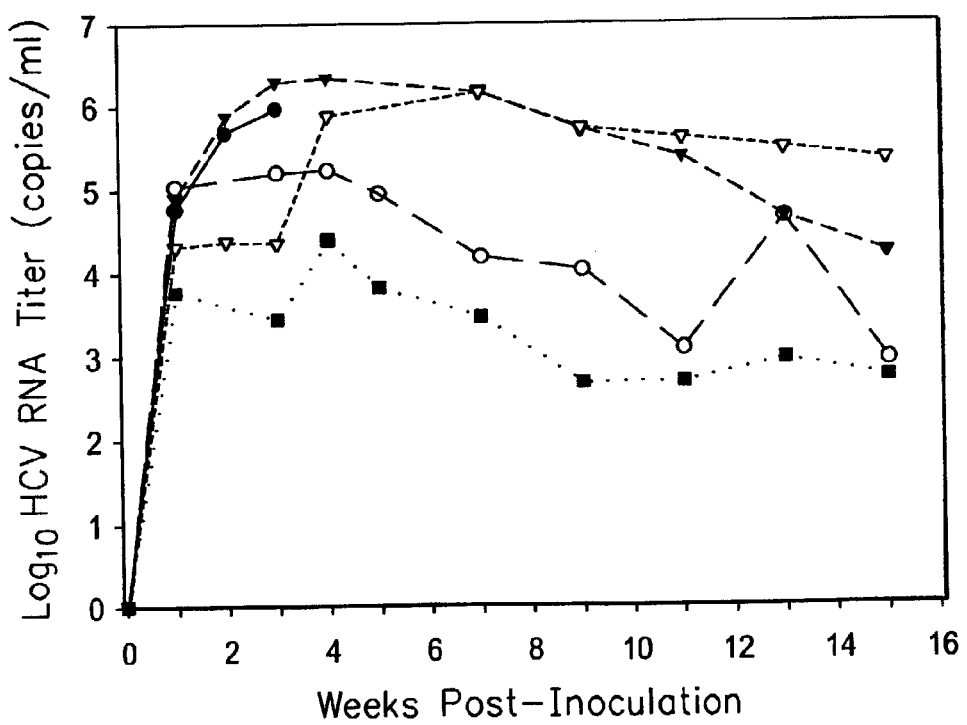
FIG. 9 is a graph showing rising serum HCV RNA titers over the first 4–7 weeks post inoculation in homozygous transgenic graft recipients after inoculation with HCV-infected human serum. Each line represents serial titers from an individual graft recipient.

Long-term persistence of viral titers in humans is the result of ongoing active proliferation. In immunocompromised chimeric animals, however, one might ascribe HCV persistence to slower viral elimination rather than true infection and replication. Five homozygous graft recipients were inoculated with 250 μl of infected human serum (genotype 3a; $2.95 \times 10^6$ viral RNA copies/ml); each animal received therefore an inoculum of $7.38 \times 10^5$ RNA copies. Results of this experiment are shown in FIG. 9. In 3/5 recipients, viral titers increased by 16-, 27- and 36-fold over the initial inoculum by 5 weeks after inoculation; in the remaining 2 recipients titers increased modestly over 5 weeks (1.6- and 4.3-fold).

Ongoing detection of positive-stranded HCV RNA has been confirmed to beyond 15 weeks after inoculation in four animals (one death after blood sampling). The initial rise in titers coupled with persistently high viral levels at 15 weeks is consistent with viral replication rather than carryover artifact. In further study, a sixth chimeric mouse was infected with a much smaller viral inoculum ($1.35 \times 10^3$ RNA copies). The total serum viral load at 10 weeks after infection was measured at $1.33 \times 10^6$ copies, a 1000-fold increase. A nonproductive "interaction" could not reasonably sustain a 3-log increase in viral load, strongly supporting the occurrence of viral replication.

HCV is a positive-stranded RNA virus replicating through a negative-stranded intermediate; detection of (−) strand HCV RNA within the liver constitutes proof of replication. To reduce the risk of false positive results (Lanford et al. Virology 202:606–614 (1994)), (−) strand analysis was performed using two separate but complementary techniques.

Eight homozygous graft recipients inoculated with $5 \times 10^5$ copies of viral RNA from freshly obtained human serum were confirmed to have (+) strand HCV RNA at 3–4 weeks post inoculation. Samples of liver tissue were obtained by 50% partial hepatectomy at 2–5 weeks post-inoculation in six animals and 12–13 weeks in the remaining two.

Analysis for (−) strand HCV RNA was performed in blinded fashion by an independent laboratory (A.R.) using a thermostable rTth reverse transcriptase RNA PCR protocol and strand-specific primers. The results, shown in FIGS. 10A–10C, confirmed the production of the HCV replicative intermediate (negative-stranded viral RNA) within the livers of transplanted and infected homozygous Alb-uPA mice. Letter designations (A through J, specified below) in FIGS. 10A–10C are control samples; number designations (1 through 10) represent individual RNA samples isolated from the livers of ten homozygous mice which were transplanted and then inoculated with HCV-infected human serum.

Figure 10A:
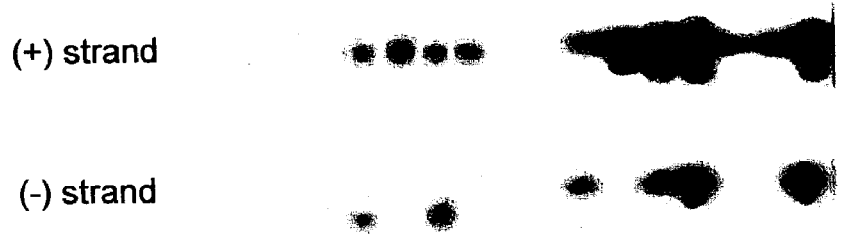
FIG. 10A is a photograph of a gel showing detection of (+) strand RNA (upper panel) or (−) strand RNA (lower panel) by thermostable rTth reverse transcriptase RNA PCR protocol with strand-specific primers. Letter designations (A through J) are control samples and number designations (1 through 10) represent individual RNA samples isolated from the livers of ten homozygous mice which were transplanted and then inoculated with HCV-infected human serum. A, wild-type control mouse, nontransplanted, noninfected; B, heterozygous transplanted mouse inoculated with HCV; C, homozygous transplanted mouse, not inoculated with HCV; D, serum taken from an infected human; E, standard DNA ladder; F, binding of labeled probe to target DNA sequences generated from (+) strand (upper panel) or (−) strand (lower panel) viral RNA; G, mouse liver RNA (10 μg) doped with serum RNA from an HCV-positive human; H, mouse liver RNA (10 μg) doped with 10⁶ copies radioinert antisense (upper) or sense (lower) riboprobe; I, mouse liver RNA (10 μg) doped with 10⁶ copies radioinert sense (upper panel) or antisense (lower panel) riboprobe; J, riboprobes hybridized with 10 μg mouse liver RNA, all subsequent steps identical except addition of RNase.

FIG. 10A shows detection of (+) strand RNA (upper panel) or (−) strand RNA (lower panel) by thermostable rTth reverse transcriptase RNA PCR protocol with strand-specific primers. A is a wild-type control mouse, nontransplanted, noninfected; B is a heterozygous transplanted mouse inoculated with HCV; C is a homozygous transplanted mouse, not inoculated with HCV; D is serum taken from an infected human; E is a standard DNA ladder; F represents binding of labeled probe to target DNA sequences generated from (+) strand (upper panel) or (−) strand (lower panel) viral RNA; G is mouse liver RNA (10 µg) doped with serum RNA from an HCV-positive human; H is mouse liver RNA (10 µg) doped with $10^6$ copies radioinert antisense (upper) or sense (lower) riboprobe; I is mouse liver RNA (10 µg) doped with $10^6$ copies radioinert sense (upper panel) or antisense (lower panel) riboprobe; J is riboprobes hybridized with 10 µg mouse liver RNA, all subsequent steps identical except addition of RNase. Fragments in this lane represent undigested riboprobe (arrow), with expected lengths greater than those of corresponding fragments protected by hybridization to their targets. Replication of the HCV genome is clearly seen in 5/9 animals assayed by this method.

Figure 10B:
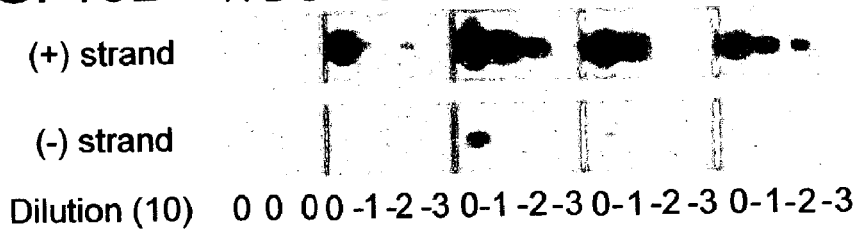
FIG. 10B is a dilution series analysis.
Figure 10C:
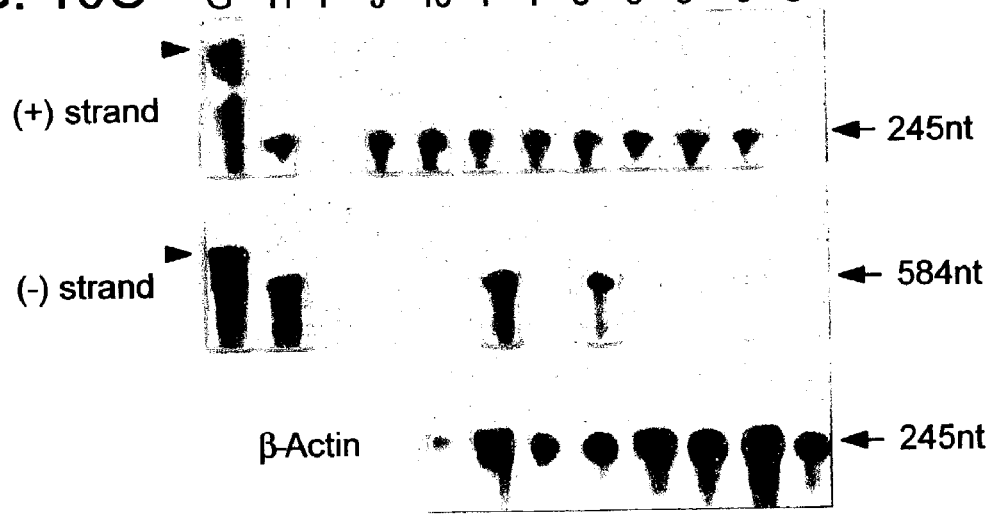
FIG. 10C is a photograph of a gel showing detection of (+) strand HCV RNA (upper panel), (−) strand HCV RNA (middle panel) or β-actin RNA (lower panel) by RNase protection assay. Control lanes are as designated above; mouse 10 was analyzed only by the RPA method. Letter and number designations are the same as in FIG. 10A.

FIG. 10B shows the results of a dilution series analysis of selected animals using the thermostable rTth reverse transcriptase RNA PCR protocol. Both (+) and (−) stranded RNA are detectable over 2–3 log dilutions. In this experiment only, (−) stranded viral RNA was not detected in mouse 5 although it was seen earlier and was confirmed later in multiple RPA analyses. The results of detection of (+) strand HCV RNA (upper panel), (−) strand HCV RNA (middle panel) or β-actin RNA (lower panel) by RNase protection assay are shown in FIG. 10C. Control lanes are as designated above; mouse 10 was analyzed only by the RPA method. This assay correlated with the above data 5/6 animals, confirming presence of the (−) strand in 3/4. Failure to detect (−) stranded RNA in mouse 6 is likely due to the reduced sensitivity of the RPA assay.

Immunohistochemical Analysis.

To confirm localization of HCV within transplanted mouse livers, sections of liver taken from homozygous mice which had been transplanted with human hepatocytes and then inoculated with HCV-infected human serum were immunostained with a monoclonal antibody against the NS3-NS4 region of the viral polyprotein. Control sections of human liver show a granular cytoplasmic appearance, with exclusion of staining from the nuclei (FIG. 11A). Areas of fibrosis and portal triad structures did not stain positive for NS3-NS4. Although the majority of hepatocytes did stain positively, there were areas of sparing. Control sections from nontransplanted mouse livers did not show any evidence at all of staining (not shown). Experimental sections taken from transplanted and infected mice (FIG. 11B) showed areas of hepatocyte staining which were similar in cytoplasmic granular appearance to control human sections, although at a slightly reduced staining intensity. This immunohistochemical finding provides evidence that HCV does truly infect human hepatocytes within the chimeric liver of a transplanted Alb-uPA mouse.

Conclusion

These separate and independently-performed assays clearly demonstrate presence of negative-stranded HCV RNA within chimeric livers sampled at 2–5 weeks post-inoculation. Experiments with sequential weekly analysis by quantitative RT-PCR (FIG. 9) demonstrated a rapid rise in HCV serum titer at weeks 2–4 after inoculation, corresponding to maximal rates of viral replication within the liver; this would be expected to be paralleled by maximal amounts of (−) stranded viral RNA. This may explain why the (−) strand is detectable earlier in infections (5/6 animals sampled at 2–5 weeks) rather than later (0/2 sampled at 12–13 weeks). Taken in combination, these data conclusively support active viral replication in this animal model. Furthermore, HCV infection is chronic. Most recently, the inventors have demonstrated an animal model of the invention based upon a chimeric, Alb/uPA transgenic mouse having a functional human hepatocyte graft (as determined by detection of high albumin serum levels at 35 weeks post-transplant (greater than about 800 units by dot blot)) and high titer HCV in serum at 35 weeks post-transplant ($1.7 \times 10^5$ copies/ml).

Serial Passage of HCV Infection

After confirming replication, serial passage of HCV infection from mouse to mouse was attempted. Fresh serum from a human donor (250 µl; $4.75 \times 10^5$ viral RNA copies) was inoculated intraperitoneally into a naïve chimeric mouse; at four weeks after inoculation, viral titers were $1.76 \times 10^6$ copies/ml. Serum taken from this mouse (125 µl; ~$2.19 \times 10^5$ RNA copies) was inoculated intraperitoneally into a second naïve chimeric mouse, which developed titers of $1.75 \times 10^4$ copies/ml at four weeks after inoculation. Serum from this first-passage recipient was then inoculated (100 µl; ~$1.75 \times 10^3$ RNA copies) into a third naïve chimeric mouse. At five weeks after inoculation, this second-passage recipient had viral titers of $3.42 \times 10^6$ copies/ml. If one assumes the null hypothesis that replication does not occur but rather the initial human inoculum persists, this second-passage recipient would have received ~6000 copies of virus from the initial inoculum ($4.75 \times 10^5$ viral copies$\times$1:8 dilution$\times$1:10 dilution, assuming mouse serum volume ~1000 µl); the second-passage recipient had 576× more measured viral RNA than would have been received from the original human inoculum. Serum from this second-passage recipient (30 µl) was inoculated into two additional naïve mice, both of whom subsequently developed HCV infections (third-passage recipients; quantitation pending). Serial transmission has thus far been demonstrated in 7 animals including 2 animals after three generations of passage. This transmission from human→mouse→mouse→mouse→mouse represents both replication of the HCV genome and production of fully-infectious particles.

These experiments establish that homozygous scid/Alb-uPA mice with chimeric human livers can be infected de novo with HCV-positive human serum, support HCV replication at clinically relevant titers, and are capable of transmitting this infection to other chimeric mice. Successful infections have been established with viral genotypes 1a, 1b, 3a and 6a, with rapid increases in viral RNA titers to levels easily detectable by standard commercial assays. Homozygosity of Alb-uPA is critical to successful establishment of viral infection, and by using homozygotes as recipients, coupled with early screening of graft function by dot blot analysis, HCV infections are routinely established in ~75% of all inoculated animals.

The transplantation procedure requires basic microsurgical equipment and technical skills. In our hands a transplant, including anaesthetic induction and recovery time, takes 5–6 minutes per animal. While access to human hepatocytes may be limiting for some investigators, the yields from hepatocyte isolations in our laboratory average $2-3 \times 10^8$ viable human cells. The ability to cryopreserve surplus cells allows for efficient utilization, as well as transportation to centers without human tissue access. While success rates have been lower after transplanting cryopreserved hepatocytes, pre-screening these recipients with dot-blot hybridization has allowed for their efficient use in HCV studies, with success in viral infection in approximately 50% of animals with dot blot>250 units at time of inoculation.

Example 5

Human Umbilical Cord Blood Cells as Source of Cells for Transplantation

In the current literature, human stem cells are proven to be pluripotent. They have the ability to regenerate into hematopoietic cells as well as hepatocytes given the proper combination of conditions and stimuli. Human stem cells have been shown to have the ability to repopulate the hematopoietic cells in NOD/SCID mice (see, e.g., Bhatia et al. *J Exp Med* 186(4):619–24 (1997); Bhatia et al *Proc Natl Acad Sci USA* 94(10):5320–5 (1997); Larochelle et al. *Nat Med* 2(12):1329–37 (1996). With regards to liver repopulation, however, clinical studies have used stem cell transplants in pediatric hepatoblastomas to regenerate liver.

Human cord blood is a rich source of stem cells. In addition, they have been reliably cryopreserved and cell integrity is preserved post-thaw. Human cord blood is also much more readily available. Because of the limited availability of fresh liver tissue, an alternate source of human hepatocytes is useful in the development of the animal model of the invention. The human cord blood cells transplanted into the SCID.bg/Alb-uPa mice of the invention can regenerate into viable human hepatocytes, and engraft and develop a chimeric mouse/human liver. In addition, the cells can populate the immune system of our SCID.bg/Alb-uPa mice.

Materials and Methods

Following the protocol described herein, SCID.bg/Alb-uPa mice are transplanted with human hepatocytes at 10–14 days of age. Instead of human hepatocytes, 5 million human cord blood monocytes (source of stem cells) are transplanted via intrasplenic injection. The protocol of testing mouse sera for the presence of human albumin via dot blot at four weeks post-transplant is followed as described herein.

In addition, to determine whether the immune system has also been repopulated, a peripheral blood smear is performed at 4 weeks of age to look for the presence of lymphocytes. At eight weeks, the serum is tested for the presence of human IgG via ELISA and the presence of CD4+ and CD8+ cells with FACS analysis. To test functionality, PHA stimulation is performed.

Example 6

Interferon Alpha-2b Treatment in Scid/uPA Mice Infected with HCV

The HCV animal models of the invention can be used to screen for anti-HCV activity of candidate chemotherapeutics. Interferon alpha-2b is known to have anti-HCV activity. Thus, treatment of HCV-infected mice of the invention with recombinant interferon alpha-2b will result in a significant decrease in the levels of HCV RNA.

Methods and Materials:

Animals: Human hepatocytes were isolated from pieces of human liver tissue obtained from the operating theater using continuous perfusion with collagenase (Liberase HI, Boehringer Mannheim). Homozygote SCID/uPA mice were transplanted with $0.5 \times 10^6$ to $1.0 \times 10^6$ fresh human hepatocytes via intrasplenic injection at 10–15 days of age. At 4 weeks post-transplant blood was drawn and assayed for human albumin (HA) concentration using a quantitative dot blot assay. Mice demonstrating >200 ug/ml of HA were considered to have a successful graft and used for this experiment.

HCV infection: At 8 weeks post-transplant, mice were injected intraperitoneally with 50 µl of serum from a HCV positive liver transplant patient, genotype 3. The serum was stored at –70 degrees Celsius and thawed out at time of inoculation. The patient serum demonstrated HCV RNA levels of $2.56 \times 10^5$ IU/ml. All HCV quantitation was performed by the Provincial Laboratory at the University of Alberta Hospital using the Cobas Amplicor HCV Monitor version 2.0 (Roche Diagnostics).

Interferon administration: The mice were divided into 3 treatment groups: group 1=controls (n=5), group 2=interferon-α2b (IFN) 135 IU/g/d (n=1), group 3=1350 IU/g/d (n=2). Treatment was started 2 weeks after HCV inoculation. The IFN (or an equivalent volume of normal saline) was injected IM for 15 consecutive days. Blood was drawn to assay for HCV RNA levels and graft function at the start of treatment, at the end of treatment, and 2 and 4 weeks after treatment had stopped.

Animals received human hepatocyte transplants and, after confirmation of satisfactory engraftment by serum dot-blot assay for human albumin of >250 units, were injected with 100 µl IP of serum from a human carrier of genotype 3 HCV. Baseline values are viral copies/ml mouse serum from 2 weeks post HCV injection, when prior studies revealed the greatest absolute rise in HCV copies. Interferon therapy was begun at baseline in 3 animals at dosages of 135 (n=1), or 1350 (n=2) IU/gram body weight/day for 2 weeks of treatment. Week 2 is HCV titre by RT-PCR at end of interferon therapy, while week 4 is 2 weeks after therapy; assay was by the Roche Amplicor kit run by the Provincial Laboratory of Public Health of Alberta. Samples were blinded and interspersed with human serum samples from clinical analyses. Assay sensitivity is 600IU/ml or approximately $1.2 \times 10^3$ viral copies/ml. The results are shown in the Table 3 below ("E" indicates the exponent value).

TABLE 3

Affect of IFN upon HCV Infection in the Animal Model of the Invention

| Treatment | HCV titre (RT-PCR) | | |
|---|---|---|---|
| | Baseline | week 2 | week 4 |
| Control | 2.7 x 10E3 | 2.5 x 10E4 | 6.6 x 10E3 |
| Control | 2.4 x 10E4 | 7.5 x 10E5 | 1.4 x 10E6 |
| Control | 1.6 x 10E5 | 1.7 x 10E5 | .9 x 10E5 |
| Control | 7.5 x 10E5 | 2.1 x 10E6 | 1.5 x 10E6 |
| Control | 1.2 x 10E6 | >2 x 10E6 | 1.7 x 10E6 |
| 135IU/g/d | 2.2 x 10E5 | 3.6 x 10E4 | 4.5 x 10E4 |
| 1350IU/g/d | 1.8 x 10E3 | ND | ND |
| 1350IU/g/d | 3.3 x 10E4 | ND | ND |

Four of five control untreated mice demonstrate rising titres of HCV over this time period, while 1 shows stable levels. All 3 treated animals demonstrated decreasing viral titres with the 2 at higher dose demonstrating viral clearance (ND=not detected).

Example 7

Passive Immunity to Hepatitis B Infection with Administration of HBIg

The HCV model described herein is based on the presence of a chimeric mouse/human liver in an immunocompromised animal, as a specific example, the SCID.bg/Alb-uPa mouse. This model not only supports a replicating hepatitis C virus, but has also supports a hepatitis B infection as well.

Because there are no currently no proven vaccinations for hepatitis C, HBV-infected mice are used to test the validity of the animal model in testing vaccinations. There are currently both passive and active immunizations available for HBV.

Hepatitis B Immunoglobulin (HBIg) is a developed passive vaccine to the hepatitis B surface antigen. It is developed by collecting and pooling the plasma from positive anti-HBs donors. The final result is a high titre anti-HBs preparation. In the clinical setting, it has limited applicability because of 1) partially effective 2) short half-life and 3) interferes with long lasting immunity. However, in certain situations, it has proven to be useful.

In liver transplantation, HBIg immunoprophylaxis is widely used and accepted. It has shown to significantly reduce the recurrence rate of HBV post-transplant in hepatitis B positive patients. Consequently, it has reduced the morbidity in both the graft and the patient. Patients are treated with a large bolus dose during the anhepatic stage of the transplant. Treatment is continued for one year and the dosage is determined by the anti-HBs antibody titre. Post needle-stick exposure, the administration of HBIg has prevented the transmission of HBV in 80% of cases.

The animal model of the invention can be used in vaccine development. As a control to demonstrate the usefulness of the animal model in vaccine development, a proven immunoprophylactic vaccine available for HBV is used. Through injections of hepatitis B immunoglobulin (HBIg), the SCID.bg/Alb-uPa mice will obtain passive immunity to a subsequent inoculation of hepatitis B, thus preventing and active viral infection.

As emphasized above, HBV and HCV are not comparable viruses. However, since there is currently no passive immunotherapy available for HCV, the use of HBV and the HBIg provides an initial screen to show that an immunotherapeutic known to be effective against HBV infection is effective in the animal model of the invention provides further evidence that the animal model in fact provides for a valuable screening tool for passive immunotherapy.

Materials and Methods

Following the protocol described in the Examples above, SCID.bg/ALB-uPa mice are transplanted with human hepatocytes at 10–14 days of age. Four weeks post-transplant, the mice are tested by dot blot for human albumin. Those animals with a strong signal are then chosen for experimental use.

Day 0: At eight weeks of age, the mice allotted into the experimental group receive a high dose intramuscular injection of HBIg (1 cc/kg) where as the control group receive a injection of normal saline.

Day 1: All mice are inoculated with 100 μL of high titre HBV serum (intraperitoneal injection).

Day 1–14: Experimental mice are treated with a maintenance dose of HBIg (comparable to that in liver transplant patients) of 0.12 cc/kg once a day. Control mice are continued on normal saline injections.

To assay the effect of HBIg, serum samples are obtained for HBV titres at 2, 4, 6, 8, 10 and 12 weeks post-HBV infection. Hepatitis B surface antibody is assayed on day 1 prior to HBV inoculation and again at eight weeks post-infection.

Example 8

Use of Immune Reconstituted HCV Animal Model to Analyze the Immune Response in HCV Infection The animal model of the invention provides a valuable tool to study human immune responses in context of autologous liver cells infected with HBV or HCV. The mice carrying human liver cells can be immune-reconstituted with autologous peripheral blood mononuclear cells (PBMCs, $2-3 \times 10^7$ cells/mouse), to provide a model system of HBV and HCV infection to perform the following studies. This model can then be used in the following exemplary ways.

The experiments described below can provide insights into the critical role of various components of immune system, e.g., antigen presenting cells, certain cytokines and T cells, and mechanisms underlying the immunomodulation in chronic hepatitis infection. These studies can provide the foundation for design and investigation of novel strategies and novel vaccine candidates for the immunotherapy of chronic hepatitis virus infections. These studies will also establish the mouse model system as preclinical model for the evaluation of future chemotherapeutic and/or immunotherapeutic treatment of chronic hepatitis infections.

Evaluation of the Immune Response and Modulation in Chronic HCV Infection

HCV infected mice, which are transplanted with human liver cells and reconstituted with autologous PBMCs, are used to evaluate overall immune cell competence and/or immune suppression in context of progressive HCV infection. A time course study is performed where splenic or lymph node T cells are obtained from the mice and set up in in vitro culture to examine response against mitogens, allogeneic APCs, promiscuous Th epitopes (e.g., tetanus toxoid, PADRE peptides etc.) are evaluated by T cell proliferation assay. In the same cultures, cytokine secretion in the culture supernatant or intracellular production is examined. In addition, in these cultured cells, T cell activation markers are examined by flow cytometry. These experiments are performed in a time course fashion, so T cells will be recovered from mice at various times (e.g., 1,4,8,12,16 weeks post infection and PBMCs reconstitution) and examined for their response to polyclonal stimuli as stated above. HCV virus load is also evaluated at each time point, so that overall immune response can be correlated with virus load.

Along with polyclonal stimulus, T cell responses against known conserved HCV promiscuous helper epitopes are examined in vitro and their stimulation correlates with virus load in time course experiments. Similarly, B cells are isolated at the same time and cultured with polyclonal B cell stimuli, e.g., LPS, α-CD40 etc. and examined for cytokine secretion as well as overall Ig production in culture upon polyclonal stimulation. Uninfected, PBMC reconstituted mice are used as controls. The overall T and B cell competencies in ongoing HCV infections can also be evaluated.

Alternatively, mice are challenged in vivo with promiscuous HCV and non-HCV Th epitopes at various times after infection and PBMCs reconstitution followed by examination of those peptide reactive T cells by cytokine production, activation marker expression and proliferation. Again, in these in vivo challenge experiments, overall T cell responses are correlated with virus load, time from infection etc. T cells obtained from the unimmunized but immune-reconstituted and HCV infected mice are evaluated for overall CD4/CD8 ratios, MHC molecules, and other T cell/activation molecules and compared with uninfected but immune reconstituted mice. In alternate experiments, normal human PBMCs are polyclonally stimulated in the presence of sera from HCV infected mice and examined for any modulation of T cell responses. Following these experiments, phosphorylation of various TCR molecules, Ca2+ mobilization etc., are examined to determine the biochemical basis of any observed T cell response defects. Additionally, we will examine whether T cells undergo apoptosis upon stimulation.

Cytokines and Immunoregulatory Molecules in Chronic Hepatitis Virus Infections.

In order to examine the role of various cytokines (type 1 vs. 2) on HCV infection, sera is collected from mice infected with HCV and reconstituted with PBMCs and examine for 1 vs. 2 type cytokines prevalence. These experiments are performed in a time course manner to correlate cytokine production with HCV virus load, and compared with control non-infected but immune reconstituted mice. On the other hand, predominant 1 or 2 type cytokines, e.g., IL-2, γ-EFN, IL-4, IL-10 and IL-12 are injected or abrogated (by injecting anti-cytokine antibodies) in these mice and their effect on virus load, T cell response to promiscuous HCV and non-HCV peptides as well as polyclonal stimulus evaluated. Additionally, progression in cytokine switch, defects in cytokine production or their modulation, are evaluated immediately after infection or after a longer time (i.e., 2–3 months in mice). In the in vitro experiments, the role of addition of certain cytokines in vitro to the T cell responses.

Antigen Presenting Cells (Dendritic Cells, DCs) in Chronic HCV Infections and Modulation of DC Function to Provide Protective Immune Responses.

There is some evidence to suggest that in chronic HCV infection in humans, dendritic cell function is impaired. The dendritic cells (DCs) are the most potent stimulators of CD4+ T cells to induce efficient immunity. Therefore, examination of DC function in context of HCV infection is essential to understand immune response against HCV infection.

From the HCV infected PBL reconstituted mice, monocytes are isolated from spleens or blood and cultured with GM-CSF and IL-4 to generate immature DCs. These immature DCs are matured in presence of γ-IFN, α-IFN, LPS or α-CD40 and examined for the expression of DC activation markers by flow cytometry, IL-12 production in the supernatant and ability to stimulate allogeneic T cells & HCV promiscuous Th epitope presentation to autologous T cells. These experiments are performed in a time course manner, and progression in change in DC function examined as a factor of time and HCV virus load.

In additional experiments, mice carrying HCV infection and reconstituted with human PBMCs are injected with in vitro activated mature DCs and examined for T cell responses and virus load.

Immunization of Promiscuous Human Helper and CTL Epitopes in HCV Infection

In numerous studies reporting Th and cytotoxic T cell (CTL) responses in chronic HCV infected individuals, a number of promiscuous Th and CTL epitopes from conserved region of HCV have been identified in vitro, suggesting that Th and CTL priming occurs in the HCV infected individuals. However, apparently this ongoing natural T cell response in itself is not sufficient to clear the virus infection and/or replication. The animal model of the invention can be used to evaluate various immunization strategies (as listed below) using known promiscuous Th and CTL epitopes to induce strong immune responses. The mice are evaluated for generation of CTL and Th cell responses after immunization. In parallel, virus load is evaluated. The animal model can thus be used to determine the appropriate modulation of Th and CTL responses to provide immunity against HCV infection.

Immunization with antigens can examined in context of particulate formulations, e.g., liposomes; modified antigen peptides, e.g., lipidated peptides; certain adjuvants and cytokine formulations as adjuvants or adjuncts; dendritic cells loaded with antigens; DNA mediated immunizations; T cell adoptive therapy with antigen specific T cells expanded in vitro; and the like.

Immunogenicity of Synthetic Peptides (or Modified Lipopeptides) Derived from Structural and Non-Structural Proteins of HBV and HCV An alternative hypothesis for the failure to resolve ongoing HCV infection in HCV chronic carriers focuses on evidence that Th and CTL responses against these epitopes are actually not able to suppress virus replication or clear virus infected cells, and immune responses against other epitope determinants are necessary to generate protective immunity. In order to determine novel T cell epitopes on HCV polyprotein, initial in silico studies are performed to identify putative Th and CTL epitopes from conserved structural as well as functional viral proteins. These identified epitopes are then modified and eavluated in the reconstituted animal model of the invention for their ability to generate strong T cell responses, indicating that they are immunotherapeutic vaccine candidates.

Examination of Combined Therapeutic Approaches (Antigen-Based Vaccines and Small Molecules that Inhibit Viral Replication and/or Induce Immunomodulation.

This approach takes into consideration the immune response in chronic HCV infection, and uses the reconstituted animal model of the invention to identify anti-viral therapeutics that take advantage of a combination of antigen-based therapies and small molecule-based therapy, where there small molecule has activity in inhibition of viral replication and/or in immunomodulation. Combinations that provide effective suppression of virus replication or virus clearance are identified using HCV infected, immune reconstituted animals as described above. Vaccine candidates are evaluated in combination with cytokines (such as IL-2 or liposomal IL-2) to provide efficient immunity to suppress and/or clear HCV infection.

Example 9

Use of the Model for Evaluation of Therapies for Hyperlipidemia

As discussed above, Apo B100 is an art-accepted marker for risk of artherosclerosis that results from hyperlipidemia. In order to assess the use of the mouse model of the invention in screening for agents that have activity against hyperlipidemia, a mouse monoclonal antibody specific for human Apo B100 was used to detect production of human apo B100 production by the engrafted human cells. Serum samples were collected from a chimeric Alb/uPA transplanted animal and from a Alb/uPA non-transplanted animal (negative control). Human serum served as a positive control. The serum was analyzed by Western blot using an anti-Apo B100 antibody according to methods well known in the art.

As shown in FIG. 12 while antibody binding to Apo B100 was not detected in the non-transplanted control animal (lane 3), antibody binding was detected in both the human serum positive control (lane 1) and the chimeric Alb/uPA transplanted animal (lane 2). These data show that Alb/uPA mouse liver with sustained human chimerism secretes human apo B100. This observation indicates that the Alb/uPA mouse model can provide a basis for development of selective treatments that decrease the amount of apo B100 from the liver and, as a consequence, decrease the risk of cardiovascular disease and stroke via atherosclerosis.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A method for evaluating liver toxicity of an agent, the method comprising the steps of:

administering a candidate agent to a chimeric, transgenic immunodeficient mouse whose genome comprises a transgene comprising a polynucleotide encoding a urokinase-type plasminogen activator polypeptide operably linked to a promoter such that the polypeptide is expressed in the mouse's liver cells, wherein the mouse is homozygous for the transgene, and the mouse further comprises a liver comprising human hepatocytes; and analyzing the effect of the candidate agent upon human liver function or human liver histology;

wherein a decrease in liver function or adverse alteration in liver histopathology in the presence of the agent, relative to the absence of the agent, indicates that the agent is toxic to human liver cells.

2. The method of claim 1, wherein human hepatocytes constitute at least about 20% of hepatocytes in the chimeric liver.

3. The method of claim 1, wherein the human hepatocytes are functional for at least about 15 weeks following transplantation into the mouse.

4. The method of claim 1, wherein the transgene comprises a nucleotide sequence encoding murine albumin promoter operably linked to a murine urokinase-type plasminogen activator.

5. The method of claim 1, wherein immunodeficiency of said transgenic immunodeficient mouse is caused by a scid mutation.

6. The method of claim 1, wherein said analyzing comprises analyzing the effect of the candidate agent upon human liver function.

7. The method of claim 1, wherein said analyzing comprises analyzing the effect of the candidate agent upon human liver histology.

8. The method of claim 6, wherein said human liver function is analyzed by assessing levels of alpha-1 antitrypsin.

* * * * *